US008097135B2

(12) United States Patent
Bakker et al.

(10) Patent No.: US 8,097,135 B2
(45) Date of Patent: *Jan. 17, 2012

(54) REVERSIBLE ELECTROCHEMICAL SENSORS FOR POLYIONS

(75) Inventors: Eric Bakker, West Lafayette, IN (US); Alexey Shvarev, Corvalis, OR (US)

(73) Assignee: Auburn University, Auburn, AL (US)

( * ) Notice: Subject to any disclaimer, the term of this patent is extended or adjusted under 35 U.S.C. 154(b) by 1070 days.

This patent is subject to a terminal disclaimer.

(21) Appl. No.: 11/494,885

(22) Filed: Jul. 27, 2006

(65) Prior Publication Data

US 2007/0017821 A1    Jan. 25, 2007

Related U.S. Application Data

(63) Continuation-in-part of application No. 10/887,251, filed on Jul. 8, 2004, now Pat. No. 7,553,403.

(60) Provisional application No. 60/485,856, filed on Jul. 9, 2003, provisional application No. 60/706,117, filed on Aug. 5, 2005.

(51) Int. Cl.
*G01N 27/327* (2006.01)
*G01N 27/333* (2006.01)

(52) U.S. Cl. ..... 204/418; 205/789; 205/792; 205/789.5; 204/296

(58) Field of Classification Search .................. 204/402, 204/403.01, 403.06, 416, 418; 205/775, 205/777.5, 778, 789, 792
See application file for complete search history.

(56) References Cited

U.S. PATENT DOCUMENTS

| 5,137,607 A * | 8/1992 | Anderson et al. ............. 205/334 |
| 5,607,567 A * | 3/1997 | Yun et al. ................... 205/777.5 |
| 6,908,542 B2 * | 6/2005 | Meyerhoff et al. ........... 205/789 |
| 2002/0115957 A1 | 8/2002 | Sun et al. ........................ 604/20 |
| 2005/0023153 A1 | 2/2005 | Bakker et al. ................. 205/775 |

FOREIGN PATENT DOCUMENTS

WO      01/88520 A2    11/2001

(Continued)

OTHER PUBLICATIONS

Badr, Ibrahim H. A., Narayanan Ramamurthy, Victor C. Yang, and Mark E. Meyerhoff. "Electrochemical Assay of Proteinase Inhibitors Using Polycation-Sensitive Membrane Electrode Detection." Analytical Biochemistry 250 (1997): 74-81.*

(Continued)

*Primary Examiner* — Kaj K Olsen
*Assistant Examiner* — Kourtney R Salzman
(74) *Attorney, Agent, or Firm* — Haverstock & Owens LLP

(57) ABSTRACT

The present invention is directed to a reversible electrochemical sensor for polyions. The sensor uses active extraction and ion stripping, which are controlled electrochemically. Spontaneous polyion extraction is suppressed by using membranes containing highly lipophilic electrolytes that possess no ion-exchange properties. Reversible extraction of polyions is induced by constant current pulse of fixed duration applied across the membrane. Subsequently, polyions are removed by applying a constant stripping potential. The sensors provide excellent stability and reversibility and allow for measurements of heparin concentration in whole blood samples via protamine titration. The sensors can also monitor a polyion concentration and an enzyme activity, wherein the polyion decomposition is directly proportional to the enzyme activity in a sample. Additionally, the sensors can monitor an enzyme inhibitor activity. Also, an immunoassay can be used to detect analytes by employing one of a polyion and an enzyme as markers.

34 Claims, 12 Drawing Sheets

FOREIGN PATENT DOCUMENTS

WO 2005/008232 A1 1/2005

OTHER PUBLICATIONS

Lutze, Oliver, Ravi K. Meruva, Aaron Frielich, Narayanan Ramamurthy, Richard B. Brown, Robert Hower, and Mark E. Meyerhoff. "Stabilized Potentiometric Solid-State Polyion Sensors Using Silver-Calixarene Complexes as Additives Within Ion-exchanger-based Polymeric Films." Fresenius J Anal Chem 364 (1999): 41-47.*

CAS information sheet from STN for ETH 500.*

* cited by examiner

REVERSIBLE ELECTROCHEMICAL SENSORS FOR POLYIONS

RELATED APPLICATIONS

This patent application is a continuation-in-part application of U.S. patent application Ser. No. 10/887,251, filed on Jul. 8, 2004 now U.S. Pat. No. 7,553,403 and entitled REVERSIBLE ELECTROCHEMICAL SENSORS FOR POLYIONS, which claims benefit of priority of U.S. Provisional Application No. 60/485,856, filed on Jul. 9, 2003. U.S. patent application Ser. No. 10/887,251, filed on Jul. 8, 2004 and U.S. Provisional Application No. 60/485,856, filed on Jul. 9, 2003, are both herein incorporated by reference in their entirety.

This patent application also claims priority under 35 U.S.C. §119(e) of the co-pending U.S. Provisional Patent Application Ser. No. 60/706,117, filed on Aug. 5, 2005, and titled ELECTROCHEMICAL DETECTION OF ENZYME ACTIVITIES USING POLYIONS AS SUBSTRATE AND POLYION-SELECTIVE REVERSIBLE ELECTROCHEMICAL SENSORS, which is incorporated herein by reference in its entirety.

FEDERALLY SPONSORED RESEARCH OR DEVELOPMENT

The research underlying this invention was supported in part with funds from National Institutes of Health (NIH) grant nos. GM071623 and EB002189. The United States Government may have an interest in the subject matter of this invention.

FIELD OF THE INVENTION

The present invention is directed to polyion sensors. The invention is further directed to membranes for use in the detection of polyions, such as protamine and heparin, and to methods of such detection through incorporation of the membranes in electrochemical cells. In particular, the invention relates to detection of polyions through forced movement of the polyions across the membrane, wherein the movement of the polyions is reversible allowing for reuse of the membrane.

BACKGROUND

In the past decade a new direction in the field of ion-selective electrodes has emerged with the development of potentiometric sensors with plasticized polymeric membranes for the detection of polyionic macromolecules. Early work in this area proposed a polymer membrane electrode containing a lipophilic anion-exchanger, which was capable of detecting the polyanion heparin. See Ma, S. C., Yang, V. C., and Meyerhoff, M. E. Anal. Chem. 1992, 64, 694. Heparin-selective polymeric membrane electrodes are further described in U.S. Pat. No. 5,236,570 and U.S. Pat. No. 5,453,171.

Heparin is a highly sulfated polysaccharide with an average charge of −70 and an average molecular weight of 15,000 Daltons. The molecular formula for one unit of a heparin compound is provided below.

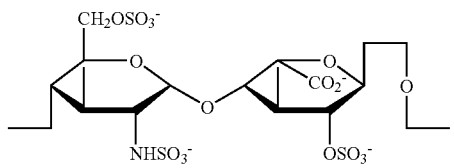

Heparin is used as an anticoagulant in major surgical and extracorporeal procedures, such as open-heart surgery, bypass surgery, and dialysis. The use of excess heparin in medical procedures can be detrimental, however, necessitating precise monitoring of heparin administration. Real-time monitoring of heparin concentration in blood is particularly useful for preventing the risk of excessive bleeding during operations and reducing postoperative complications. Activated clotting time measurement (ACT) is a common method for estimating the heparin concentration in whole blood. Although this method is widely used, it is nonspecific and indirect, and the results can be affected by many variables. In contrast to ACT, the heparin-selective electrode is able to detect heparin concentration directly in whole blood or plasma samples.

Similarly, an electrode for sensing the polycation protamine has also been proposed. See Yun, J. H., Meyerhoff, M. E., and Yang, V. C. Anal Biochem. 1995, 224, 212. The polypeptide protamine is generally used for neutralization of heparin activity (i.e. to promote coagulation). Protamine, which is illustrated below, is a polycation with an average charge +20 and is rich in arginine residues.

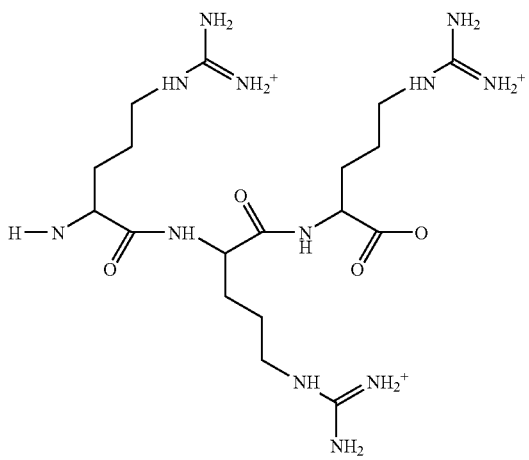

The basic guanidinium groups of protamine complex electrostatically with the sulfonate groups of heparin to render the anticoagulant activity of the heparin ineffective. Excess use of protamine, however, can also be detrimental. For example, the use of protamine frequently results in adverse hemodynamic and hematologic side effects, such as hypertension, depressed oxygen consumption, thrombocytopenia with pulmonary platelet sequestration, and leukopenia. It is therefore useful to be able to accurately detect and measure protamine concentration in biological fluid, such as blood.

Reliable detection of protamine allows for careful administration of the agent, thereby avoiding the associated problems noted above. Further, with the ability to detect protamine via ion-selective electrodes, it is also possible to determine the heparin concentration in a sample via titration of the sample with protamine. This is possible due to the specific heparin-protamine interactions described above. Such action is also described by Ramamurthy, et al., *Clin. Chem.* 1998, 606.

The observed response of the heparin-specific membrane electrode known in the art could not be explained in terms of classic equilibrium approach. The Nernst equation should yield a slope of the electrode function of less than 1 mV/decade and 2 mV/decade for heparin and protamine respectively, because of the high charge of these ions. A quasi-steady-state model to explain this unusual mechanism was subsequently described. See Fu, B. et al., *Anal Chem.* 1994, 66, 2250. The potentiometric polyion sensor response is kinetic in nature. A strong flux of polyions occurs both in the aqueous solution and the membrane phase due to the spontaneous extraction of polyions into the polymeric membrane and the concomitant exchange with hydrophilic ions from the membrane, which results in a potential change in the presence of polyions.

Because the extraction of polyions is an irreversible process when using the heparin-specific membrane electrode of the prior art, a strong potential drift is normally observed. After a relatively short time in contact with a polyion solution the sensor starts to lose its response. Extracted polyions must be removed from the membrane phase by reconditioning of the sensor, such as in concentrated sodium chloride solution. Multiple methods have been proposed in the art for overcoming response loss due to polyion concentration at the membrane surface. A pH cross-sensitive potentiometric heparin sensor has been proposed, wherein the sensor contains an ion-exchanger and a charged H+ ionophore. According to this method, heparin stripping could be accomplished by adjusting the pH of the sample. Another approach for overcoming lost sensor response is to use disposable sensors.

Thus, despite the existence of a selective extraction principle, it has been impossible thus far to design a reversible polyion sensor. Accordingly, while polyion sensors can be highly useful in critical care applications, their use is limited by the quick loss of response of the sensor. Single use sensors lead to increased expense, and the necessity of removing the sensor and reconditioning the sensor by a separate methods is overly time consuming and adversely limiting on the usefulness of the sensor. Therefore, it would be useful to have a sensor for detecting polyions that is fully reversible, wherein such reversal can be performed quickly, repeatedly, and without removing the sensor to a separate solution.

SUMMARY OF THE INVENTION

The present invention provides reversible electrochemical sensors for polyions. The sensors incorporate a potentiometric response mechanism for determining the concentration of the polyion analyte, but the processes of extraction and ion stripping are controlled electrochemically. Spontaneous polyion extraction is suppressed by using membranes containing highly lipophilic electrolytes that possess no ion-exchange properties. Reversible extraction of polyions is induced if a constant current pulse of fixed duration is applied across the membrane electrode of the invention. Subsequently, polyions are removed by applying a constant stripping potential. This ability to strip the polyions, effectively regenerating the sensor, solves the problem faced by previously proposed polyion sensors that were prone to drifting and required prolonged contact with concentrated salt solutions to strip the polyions from the sensing membrane before another measurement could be taken.

Membranes comprising the lipophilic electrolytes can be used with electrochemical cells for continuous measurement of polyion concentration in a sample solution without removing the electrode for reconditioning or replacing the electrode. Accordingly, titrations of polyions, such as heparin, are possible. For example, determination of heparin concentration in whole blood samples is possible using protamine titration.

According to one aspect of the present invention, there is provided a polyion-selective membrane for use in an electrochemical cell, wherein the membrane comprises a lipophilic electrolyte having a lipophilic cation component and a lipophilic anion component. Preferentially, one of the lipophilic cation component and the lipophilic anion component is selective for a specific polyion. Polyions that are particularly desirable for detection according to the present invention are heparin and protamine. Additional polyions that may be detected with the membrane of the present invention include deoxyribonucleic acids (DNA), ribonucleic acids (RNA), humic acids, carrageenans, and other polyionic macromolecules.

As noted above, one of the lipophilic cation component and the lipophilic anion component of the lipophilic electrolyte is selective for a particular polyion. Accordingly, in one embodiment of the invention, the lipophilic electrolyte comprises a lipophilic anion component that is selective for protamine. Preferentially, in this embodiment, the lipophilic electrolyte is tetradodecylammonium 1,3-dinonylnaphthalene-4-s-ulfonate (TDDA-DNNS). Similarly, in another embodiment, the lipophilic electrolyte comprises a lipophilic cation component that is selective for heparin. Preferentially, in this embodiment, the lipophilic electrolyte is dodecylguanidinium tetrakis(p-chlorophenyl)borate (DDG-TCIPB).

In another embodiment of the invention, there is provided a polyion-selective membrane comprising a polymeric film-forming material, a plasticizer, and a lipophilic electrolyte having a lipophilic cation component and a lipophilic anion component, wherein one of the lipophilic cation and lipophilic anion components is selective for a specific polyion. Preferentially, the polymeric film-forming material is polyvinyl chloride and the plasticizer is 2-nitrophenyl octyl ether.

In still another embodiment according to the present invention, a polyion-selective membrane for use in an electrochemical cell is provided, wherein the membrane comprises a microporous hydrophobic substrate having dispersed therein an admixture that comprises a plasticizer and a lipophilic electrolyte having a lipophilic cation component and a lipophilic anion component. Preferentially, one of the lipophilic cation component and the lipophilic anion component is selective for a specific polyion.

In another aspect of the invention, there is provided a polyion-selective membrane electrode for use in an electrochemical cell. In one embodiment, the polyion-selective membrane electrode comprises a housing, a reference solution contained within the housing, and an electrode operatively positioned within the housing such that the electrode is in contact with the reference solution. Further, according to this embodiment, a polyion-selective membrane is disposed at one end of the housing. The membrane is in contact with the reference solution within the housing, and the membrane is operatively positioned for contacting a sample solution that is external to the housing. The membrane comprises a lipophilic electrolyte having a lipophilic cation component and a lipophilic anion component, wherein at least one of the lipophilic anion and lipophilic cation components is selective for a specific polyion.

In another aspect of the present invention, there is provided a method of measuring the concentration of a polyion species in a sample solution. The method according to this aspect of the invention is capable of electrochemically controlled, reversible transport of the polyion species across a membrane. Therefore, the method is useful for continuous measurement of the concentration of a polyion species in a sample solution, such as a biological sample.

According to one embodiment of the method, there is provided a sample solution having therein a polyion species. Preferentially, the sample solution further comprises a background electrolyte. The solution is contacted with a reference electrode and a membrane electrode that are electrically connected. The membrane of the membrane electrode is comprised of a lipophilic electrolyte having a lipophilic cation component and a lipophilic anion component, at least one of the lipophilic anion and lipophilic cation components being selective for the polyion species. When the sample solution is in contact with the electrodes, an external current pulse is applied to a circuit comprising the membrane electrode and the sample solution, the applied current driving transport of the polyion species from the sample solution into the membrane. Preferably, the external current pulse is of fixed duration. A measurement of the potentiometric response between the membrane electrode and the reference electrode can be taken during the current pulse. The concentration of the polyion species is then capable of being calculated as a function of the potentiometric response.

In another embodiment of this aspect of the present invention, the method further comprises applying an external electrode potential to the membrane electrode and the reference electrode, thereby driving transport of the polyion species from the membrane. In this embodiment, the method allows for a reversible sensor, wherein the polyion is back-extracted, the membrane thus being reconditioned for further use.

In still another embodiment of the invention according to this aspect, a method of measuring the concentration of a polyion species in a sample solution is provided. The method comprises the following steps:

a) providing a sample solution comprising a polyion species and a background electrolyte;

b) providing an electrochemical cell apparatus comprising i) a polyion-selective membrane electrode comprising a membrane that comprises a lipophilic electrolyte having a lipophilic cation component and a lipophilic anion component, wherein at least one of the lipophilic anion and lipophilic cation components is selective for a specific polyion, ii) a reference electrode electrically connected to the membrane electrode, iii) a counter electrode electrically connected to the membrane electrode, iv) an electrochemical instrument operatively connected to the electrodes, and v) a controller device in communication with the electrochemical instrument;

c) contacting the sample solution with the electrodes of the electrochemical cell apparatus;

d) applying an external current pulse of fixed duration to a circuit comprising the membrane electrode, the counter electrode, and the sample solution;

e) measuring a potentiometric response during the current pulse;

f) calculating the concentration of the polyion species as a function of the potentiometric response; and g) applying an external electrode potential to the membrane electrode and the reference electrode, thereby driving transport of the polyion species from the membrane. In a preferred embodiment, steps d) through g) are repeated to obtain one or more additional measurements of the concentration of the polyion species.

According to another aspect of the present invention, there is provided an electrochemical cell apparatus. The apparatus is useful for measuring the concentration of a polyion in a sample solution. The apparatus according to one embodiment comprises: a polyion-selective membrane electrode comprising a membrane comprising a lipophilic electrolyte having a lipophilic cation component and a lipophilic anion component, wherein at least one of the lipophilic anion and lipophilic cation components is selective for a specific polyion; a reference electrode electrically connected to the membrane electrode; and an electrochemical instrument operatively connected to the membrane electrode and reference electrode.

In another embodiment according to this aspect of the invention, the electrochemical cell apparatus further comprises a counter electrode electrically connected to the membrane electrode.

In yet another embodiment according to this aspect of the invention, the electrochemical cell apparatus further comprises a controller device in communication with the electrochemical instrument. In a preferred embodiment, the controller device is a computerized controller. Such controller allows for partial or full automation of the electrochemical cell apparatus.

In another aspect of the present invention, a sensor is disclosed. The sensor comprises an electrode positioned within a housing. A membrane is disposed at one end of the housing and in contact with a sample solution external to the housing. The membrane detects a polyion concentration within the sample solution, and a rate of decomposition of the polyion concentration is directly proportional to an enzyme activity within the sample solution.

The electrode can be a Ag/AgCl electrode. The membrane can have a surface area of about 10 mm$^2$ to about 100 mm$^2$. Alternatively, the membrane can have a surface area of about 20 mm2 to about 50 mm2. The membrane can have an average thickness of about 10 μm to about 1000 μm. Alternatively, the membrane can have an average thickness of about 20 μm to about 300 μm. The polyion concentration can be that of protamine. The enzyme activity can be that of trypsin.

In another aspect of the present invention, a method of detecting a polyion concentration in a sample solution is disclosed. The method comprises the step of providing a sample solution. The method also comprises the step of contacting the sample solution with a membrane, wherein the membrane detects a polyion concentration within the sample solution, and wherein a rate of decomposition of the polyion concentration is directly proportional to an enzyme activity within the sample solution. The sample solution can comprise a biological component. The sample solution can comprise blood.

In another aspect of the present invention, a reversible electrochemical cell apparatus is disclosed. The cell apparatus comprises a polyion-selective membrane electrode, including a membrane. The membrane can detect a polyion concentration within the sample solution, and a rate of decomposition of the polyion concentration is directly proportional to an enzyme activity within the sample solution. The cell apparatus also includes means for applying a potential to clear the membrane. The means for applying a potential to clear the membrane can be an external electrode potential applied between a reference electrode and the polyion-selective membrane electrode.

In another aspect of the present invention, a reversible electrochemical cell apparatus is disclosed. The cell apparatus includes a polyion-selective membrane electrode, including a membrane. The membrane detects a polyion concentration with a solution. The cell apparatus also includes means for applying a potential between a reference electrode and the polyion-selective membrane electrode to clear the membrane.

In another aspect of the present invention, a sensor is disclosed. The sensor includes an electrode positioned within a housing. The sensor also includes a membrane disposed at one end of the housing and in contact with a sample solution external to the housing. The membrane can monitor an enzyme activity and a corresponding enzyme inhibitor activity in the sample solution.

The corresponding enzyme inhibitor activity can be one of α1-antiproteinase inhibitor, α2-macroglobulin, aprotinin, and a soybean inhibitor. A potential decrease of the present invention can be dependent on the concentration of the corresponding enzyme inhibitor in the sample solution.

In another aspect of the present invention, an immunoassay is disclosed. The immunoassay can detect analytes by employing one of a polyion and an enzyme as markers.

DETAILED DESCRIPTION OF THE EMBODIMENTS

Figure 1:
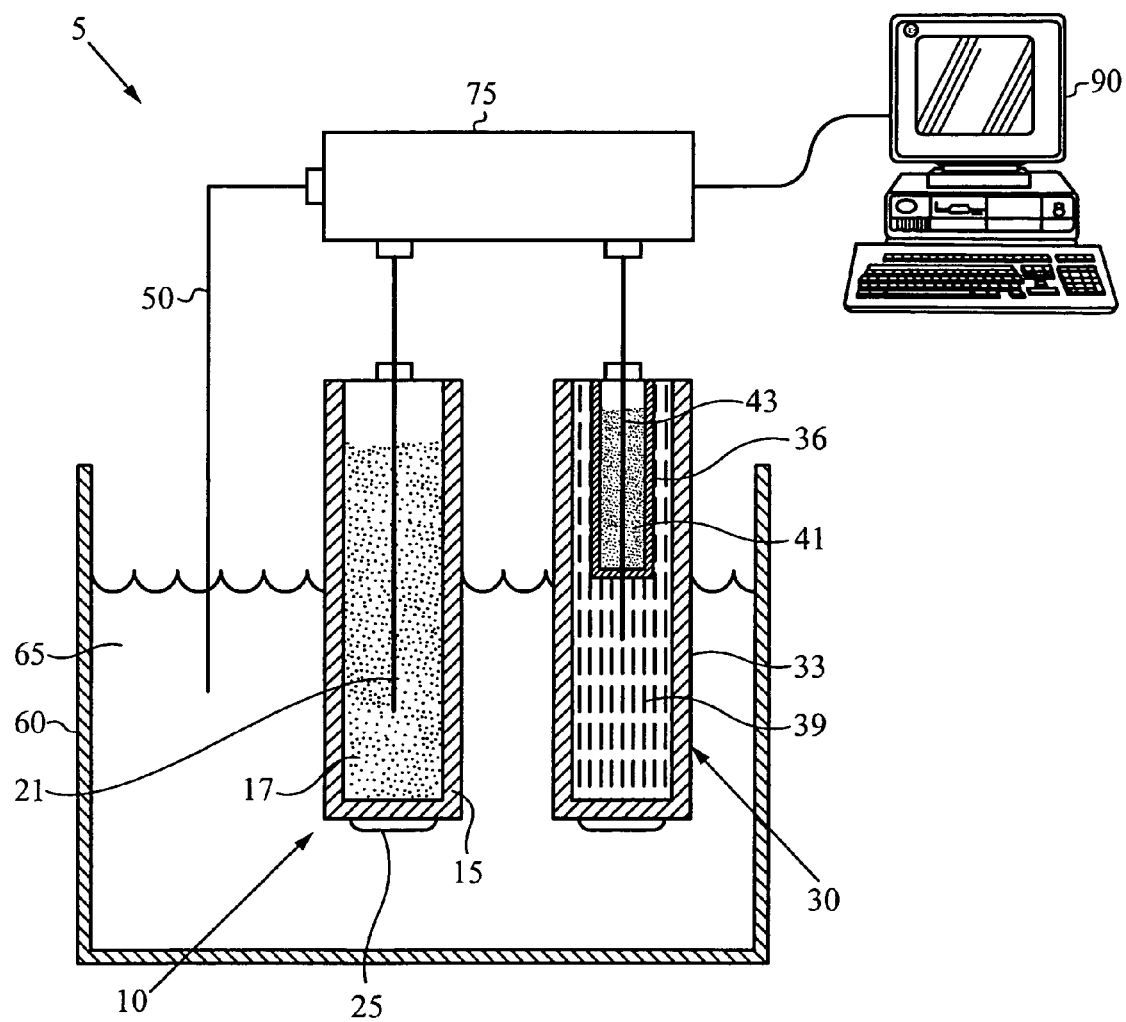
FIG. 1 is a schematic view of an electrochemical cell apparatus including a polyion-selective membrane electrode according to a preferred embodiment of the present invention.

The present invention now will be described more fully hereinafter. However, this invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise.

The present invention provides a reversible polyion sensor that combines the process of mass transport limited polyion extraction during measurement with subsequent back-extraction for reconditioning under sequential instrumental control. The invention uses a polyion-selective membrane comprising a lipophilic electrolyte. The instrumental control of ion fluxes across the membrane allows one to repeatedly extract ions into the membrane and strip ions from the membrane, yielding highly reproducible sensor responses. Further, the ability to rehabilitate the sensor membrane quickly, and during testing procedures, allows for continuous functioning to provide real-world values for polyion concentrations in solution.

Potentiometric polyion-selective sensors previously known in the art are passive sensors. Such sensors have membranes that contain lipophilic cation-exchanger molecules (generally described by the formula $R^-Na^+$) and an aqueous solution of an electrolyte. The phase boundary potential between a sample and the membrane in such a sensor may be determined according to equation (1):

$$E_{PB} = E^0 + \frac{RT}{F} \ln \frac{a_{Na}}{[Na^+]_{pb}} \quad (1)$$

wherein $a_{Na}$ is the activity of sodium ions in the aqueous solution, $[Na^+]$ is the so-called free concentration of sodium ions at the phase boundary of the membrane phase and $E^0$ incorporates the free energy of transfer for sodium from water to the membrane phase. The terms R and T are the gas constant and the absolute temperature, respectively. In the absence of protamine (or other polycation) in the sample, and by neglecting ion-pairing, the concentration of sodium ions in the membrane phase is determined by the total concentration of the lipophilic cation-exchanger, $R_T$, which can be calculated according to equation (2).

$$[Na^+]_{pb} = R_T \quad (2)$$

Consequently the membrane behaves like an ion-exchanger based sodium electrode and a Nernst response slope is expected.

If protamine is present in the aqueous solution, a strong flux of the protamine cations occurs both to the surface and into the membrane phase, forming two stagnant diffusion layers. Because the diffusion in the stagnant layer of the aqueous phase is the rate-limiting step, a quasi-steady-state diffusion may be observed at the interface. Protamine cations displace the sodium cations from the membrane phase boundary. This ion-exchange process reduces the concentration of sodium ions in the membrane phase and increases the observed potential, as calculated in equation (1). This increase in observed potential can be accounted for because the total concentration of cations in the system must satisfy the electroneutrality condition as described by equation (3)

$$[Na^+]_{pb} = R_T - z[PA^{z+}]_{pb} \quad (3)$$

where $[PA^{z+}]_{pb}$ is the concentration of protamine with charge z in the membrane phase boundary. That concentration can be formulated as a function of the bulk protamine concentration on the basis of a pseudo steady-state flux consideration calculated according to equation (4), $$[PA^{Z+}]_{pb} = \frac{D_{aq,PA} \delta_m}{D_{m,PA} \delta_{aq}} c_{PA,bulk} \quad (4)$$

where $D_m$, $D_{aq}$, $\delta_m$ and $\delta_{aq}$, are diffusion coefficients of protamine in the membrane phase, aqueous solution, and resulting diffusion layer thickness respectively. Equation (4) may now be inserted into equation (3) and equation (1) to obtain the protamine response at low concentrations. The resulting equation (5) is provided below.

$$E_{PB} = E^0 + \frac{RT}{F} \ln \frac{a_{Na}}{R_T - \frac{zD_{aq,PA} \delta_m}{D_{m,PA} \delta_{aq}} c_{PA,bulk}} \quad (5)$$

As can be determined in the above calculations, if $a_{Na}$ is fixed, the phase boundary potential of the membrane shows a direct response for protamine. Accordingly, at high protamine concentration, the sodium ions are quantitatively replaced from the membrane and a near-Nernstian response slope for protamine is expected. Such a quantitative replacement also occurs with dilute protamine solutions but requires prolonged exposure (ca. 24 h). The resulting response slope is too small to be analytically useful.

Such spontaneous ion extraction sensors suffer from the problems previously described, such as signal drift upon prolonged use and the limitation to a single use for most sensors. Accordingly, until the present invention, there was not an easy, reliable method for reconditioning the sensor allowing for continuous use.

In contrast to the passive potentiometric sensors described above that rely on spontaneous ion exchange in the ion-extraction process, the present invention electrochemically induces ion extraction by applying a constant current pulse. In order to prevent spontaneous extraction, the membrane contains a highly lipophilic electrolyte that can generally be defined according to the formula $R^+ R^-$ and does not possess intrinsic ion-exchange properties. This being the case, the initial concentrations of protamine or sodium cations in the membrane bulk is assumed to be zero. An applied cathodic current i induces a net flux of cations J in the direction of the membrane phase. To simplify the resulting equation, it can be assumed that only sodium and protamine ions can be extracted into the membrane phase. Accordingly, the relationship between current i and the fluxes of sodium, $J_{Na}$, and protamine, $J_{PA}$, can be calculated according to equation (6).

$$i = FAJ_{Na} + zFAJ_{PA} \quad (6)$$

where A is the exposed membrane area. Assuming linear concentration gradients for simplicity and recalling that the sodium concentration in the membrane bulk is zero, the sodium flux can be related to the concentration gradient across the organic phase boundary as follows in equation (7).

$$J_{Na} = -\frac{D_{m,Na}}{\delta_m} [Na^+]_{pb} \quad (7)$$

If no protamine is present, equation (6) and equation (7) may be inserted into equation (1) to give equation (8) shown below.

$$E_{PB} = E^0 + \frac{RT}{F} \ln \frac{FAD_{m,Na}}{i \delta_m} a_{Na} \quad (8)$$

A cathodic current pulse of fixed duration and magnitude, followed by a potentiostatic stripping pulse to keep the membrane bulk void of sodium ions, will give a near-Nernstian electrode slope. If protamine is present in the sample solution, the protamine will effectively compete with the sodium ions in the extraction process. Equation (6) can be rewritten in analogy to equation (7) as follows in equation (9).

$$i = -FA \frac{D_{m,Na}}{\delta_m} [Na^+]_{pb} - zFA \frac{D_{m,PA}}{\delta_m} [PA^{Z+}]_{pb} \quad (9)$$

Assuming now that the applied current imposes a flux that is always larger than the flux that can be sustained by polycation diffusion alone, equation (4) is still valid and can be inserted into equation (9). As a result, the sodium flux, $J_{Na}$, is decreased, which increases the potential according to equation (1). Inserting equation (4) into equation (9), solving for $[Na^+]_{pb}$, and substituting into equation (1) therefore yields the predicted protamine response at low polyion concentrations, which is provided below in equation (10).

$$E_{PB} = E^0 + \frac{RT}{F} \ln \frac{a_{Na}}{\frac{\delta_m}{D_{m,Na}} \left( \frac{-i}{FA} - z \frac{D_{aq,PA}}{\delta_{aq}} c_{PA,bulk} \right)} \quad (10)$$

There are differences between equation (10) and the protamine response shown in equation (5) for a potentiometric sensor as known in the prior art. Importantly, the diffusion layer thickness in the membrane phase is now dictated galvanostatically, and potentiostatic membrane renewal between pulses assures repeatable $\delta_m$ values from pulse to pulse. While the embodiments provided in the present invention use a current primarily chosen to give a maximum potential range, the invention is not intended to be so limited. Accordingly, the magnitude of the applied current pulse can be used to adjust the measuring range for polyion response. Since the applied current, and not an ion-exchanger, dictates the extraction of sodium ions into a pulsed chronopotentiometrically controlled membrane, the diffusion coefficient in the membrane phase does not influence the protamine response range. This is in contrast with the prior art potentiometric sensors governed by formula (5), where a direct dependence between competitive extraction of sodium by protamine and the membrane diffusion coefficients is known to exist.

With the above background theory in place, one can now easily see the advantages provided by the present invention. In particular, the present invention provides a polyion-selective membrane for use in an electrochemical cell. Further, the polyion-selective membrane can be an integral part of an electrochemical cell electrode. The polyion-selective membrane and the membrane electrode can be used in a reversible method of measuring the concentration of a polyion species in a sample solution.

The polyion-selective membranes of the present invention are characterized by comprising a lipophilic electrolyte having a lipophilic cation component and a lipophilic anion component, wherein at least one of the lipophilic anion and lipophilic cation components is selective for a specific polyion. The term lipophilic is generally understood to describe a species having an affinity for fat and having high lipid solubility. Lipophilicity is a physicochemical property that describes a partitioning equilibrium of a particular species between water and an immiscible organic. Lipophilicity can further be described as the ability of a species to dissolve in a lipid phase when an aqueous phase is also present. This relationship (i.e. the partition coefficient) can be defined as the equilibrium constant of the concentrations of the species in the two phases. The standard for comparison is generally a 1-octanol/water partition coefficient. The partition coefficient can be calculated according to equation (11) shown below.

$$P = \frac{[molecule]_{lipid}}{[molecule]_{water}} \quad (11)$$

According to equation (11), molecules exhibiting a high lipophilicity would be expected to show preference for solubility in a lipid rather than in water.

One functional test for determining lipophilicity is to place the compound to be tested in a container holding a mixture of 50% water and 50% lipid (such as 1-octanol). The compound of interest can be placed in the container, and a mixing force can be applied to force distribution of the compound in both phases. The container can then be allowed to rest such that the compound is allowed to come to a concentration equilibrium between the phases. The concentration of the compound in each phase can then be measured, and the concentrations can be used in equation (11) for determining lipophilicity.

Computer software can also be used to determine the lipophilicity of a species. One example of a computer program for determining lipophilicity is the ALOGPS program available online at http://146.107.217.178/lab/alogps. Principles surrounding lipophilicity are also discussed by Bakker, E. and Pretsch, E., "Lipophilicity of tetraphenylborate derivatives as anionic sites in neutral carrier-based solvent polymeric membranes and the lifetime of corresponding ion-selective electrochemical and optical sensors" *Analytica Chimica Acta*, 1995, 309, 7-17, which is incorporated herein by reference in its entirety.

Generally, a compound with a calculated P value greater than 100,000 is considered to be highly lipophilic, and therefore useful according to the present invention. Using compounds having even higher P values, however, can generally be expected to lead to sensors having increased lifetimes. Accordingly, it is preferred that the lipophilic compounds used according to the present invention have a P value of greater than 100,000, more preferably, greater than 1,000,000, and most preferably, greater than 10,000,000.

Polyion-selective membranes known in the prior art include a lipophilic electrolyte and a hydrophilic counter cation (i.e., $R^-Na^+$). According to the present invention, the hydrophilic counterion is replaced by a lipophilic counterion. Accordingly, the polyion-selective membrane of the present invention comprises a lipophilic electrolyte having a lipophilic cation component and a lipophilic anion component (i.e. $R^- R^+$). By using two lipophilic electrolytes, the lipophilic counterion may no longer spontaneously exchange with the polyion species being measured in the sample. Preferably, one of the lipophilic anion and lipophilic cation components is selective for a specific polyion, facilitating sensing of that polyion. Non-limiting examples of specific polyions for which sensing is desired include protamine, heparin, humic acids, carrageenans, deoxyribonucleic acids, ribonucleic acids, and other polyionic macromolecules.

In one embodiment of the present invention, the lipophilic anion component of the lipophilic electrolyte is selective for protamine. Protamine selectivity of the lipophilic anion component is dependant upon the functional groups of the anion. Protamine contains basic guanidinium groups (i.e., arginine residues). Therefore, in order to be selective for protamine, the lipophilic anion must include functional groups capable of forming ion pairs with the guanidinium groups of protamine. In a preferred embodiment, lipophilic anions having carboxylic (COOH), sulfonic ($SO_3H$), or sulfuric ($OSO_3H$) groups are used for protamine selectivity. In a particularly preferred embodiment, the lipophilic anion component of the lipophilic electrolyte is selected from the group consisting of 1,3-dinonylnaphthalene-4-sulfonate, 2,6-dinonylnaphthalene-4-sulfonate, dodecylbenzenesulfonate, and 3,9-diethyl-6-tridecylsulfate. Chemical formulas for these compounds are shown below.

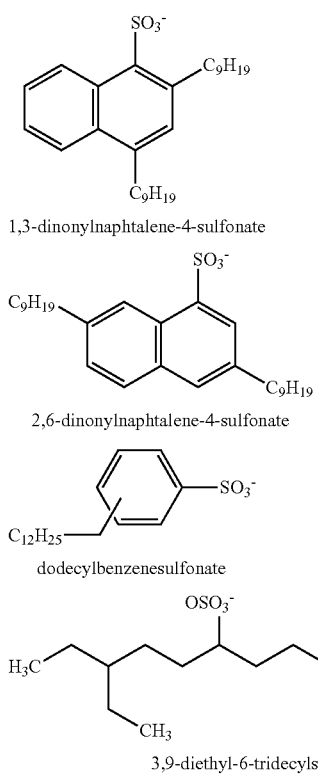

1,3-dinonylnaphtalene-4-sulfonate 2,6-dinonylnaphtalene-4-sulfonate dodecylbenzenesulfonate 3,9-diethyl-6-tridecylsulfate As described above, when the hydrophilic counterion of known membrane electrolyte materials is replaced with a second lipophilic electrolyte, the spontaneous extraction of ions from a sample into the polyion-selective membrane is prevented. Generally, the hydrophilic counterion is sodium, since sodium is the most abundant counterion present in sample solutions. The sodium ions are replaced with a lipophilic counterion by chemical synthesis. When the polyion-selective anion is selective for protamine, it is expected that any lipophilic quaternary ammonium cation with an alkyl side arm chain length of about 4 to about 16 would be a suitable counterion.

In a preferred embodiment, the lipophilic counterion paired with the protamine-selective lipophilic anion is a cation selected from the group consisting of tetradodecylammonium, tridodecylmethylammonium, and dodecyltrimethylammonium. The chemical formulas for these cations are shown below.

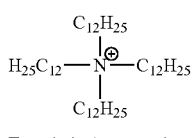

Tetradodeclyammonium

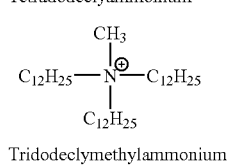

Tridodeclymethylammonium

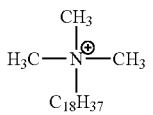

Dodecyltrimethylammonium

According to the above description of lipophilic ions, it is possible to select a combination of a lipophilic anion selective for protamine and a lipophilic counter cation to suppress the spontaneous ion exchange with the sample solution. Therefore, a protamine-selective lipophilic electrolyte for use according to the present invention could be selected from any of the possible combinations of the protamine-selective anions and the counter cations provided above. According to one preferred embodiment, the lipophilic electrolyte for use in selectively extracting protamine from a solution is tetradodecylammonium 1,3-dinonylnaphthalene-4-sulfonate (TDDA-DNNS).

In another embodiment according to the present invention, the lipophilic electrolyte comprises a lipophilic cation component that is selective for heparin. Heparin selectivity of the cation component is dependant upon the functional groups of the compound. Heparin contains sulfonic and carboxylic groups. Therefore, in order to be selective for heparin, a suitable cation must contain one or more groups that can form ion pairs with the sulfonic and carboxylic groups of the heparin. Particularly useful in providing heparin selectivity are guanidinium groups. Further, heparin extracted from a sample into an organic sensing phase (such as a membrane according to the present invention) is stabilized by stacking via long aliphatic side chains or aromatic rings of neighboring cations. Therefore, cations with high lipophilicity can be prepared by attaching one or more guanidinium groups to an aliphatic chain having a chain length of about 4 to about 18 carbon atoms and/or suitable aromatic functionalities. In a preferred embodiment, the lipophilic cation component of the lipophilic electrolyte is selected from the group consisting of dodecylguanidinium and N,N'-1,10-decanediylbis(guanidinium). The chemical formulas for these cations are shown below.

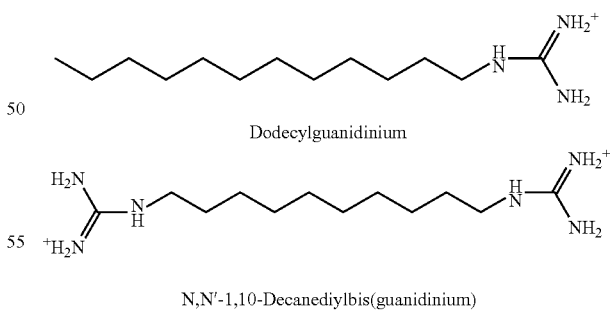

Dodecylguanidinium

N,N'-1,10-Decanediylbis(guanidinium)

Again, when the hydrophilic counterion is replaced with a second lipophilic electrolyte, the spontaneous extraction of ions from a sample is prevented. Generally, the most abundant anion in test solutions, chloride, is replaced via chemical synthesis with a lipophilic anion. One group of anions useful as counterions according to this embodiment are tetraphenylborate derivatives, such as the three borates provided below.

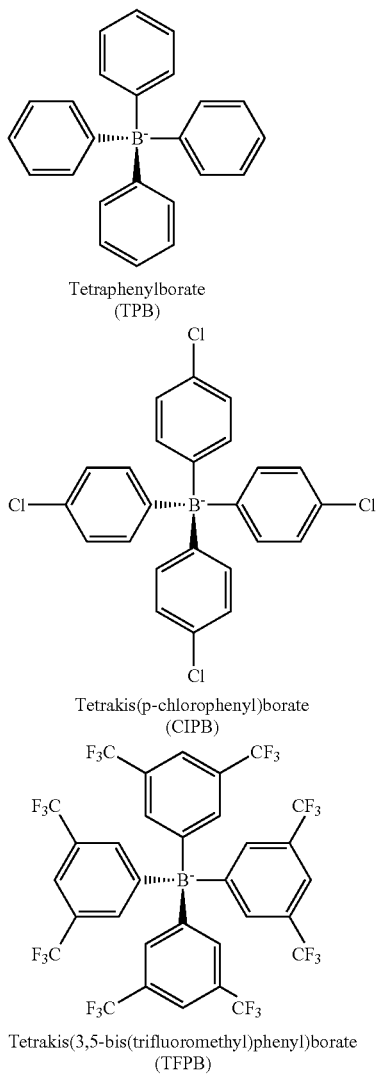

Tetraphenylborate
(TPB)

Tetrakis(p-chlorophenyl)borate
(ClPB)

Tetrakis(3,5-bis(trifluoromethyl)phenyl)borate
(TFPB)

Another suitable group of anions is lipophilic (perhalogenated or alkylated) dodecacarboranes. Dodecacarboranes are based upon the icosahedral carborane anion which, in its fully unsubstituted form, has the chemical formula $CB_{11}H_{12}^-$. Halogenated dodecacarboranes, such as $1\text{-H}—CB_{11}Cl_{11}$, $1\text{-H}—CB_{11}Br_{11}$, and $1\text{-H}—CB_{11}I_{11}$, are especially useful according to the present invention and are more fully described by Peper, S. et al., "Ion-pairing. Ability, Chemical Stability, and Selectivity Behavior of Halogenated Dodecacarborane Cation Exchangers in Neutral Carrier-Based Ion-Selective Electrodes," *Analytical Chemistry*, (2003) 75(9), 2131-2139, which is incorporated by reference in its entirety. Also useful according to the present invention are alkylated dodecacarboranes, wherein the halogen groups as described above are replaced various alkyl groups. In a preferred embodiment, the hydrophilic counterion paired with the heparin-selective lipophilic cation is a tetrakis(p-chlorophenyl) borate anion.

According to the above description of lipophilic ions, it is possible to select a combination of a lipophilic cation selective for heparin and a lipophilic counter anion to suppress the spontaneous ion exchange with the sample solution. Therefore, a heparin-selective lipophilic electrolyte for use according to the present invention could be selected from any of the possible combinations of the heparin-selective cations and the counter anions provided above. According to one preferred embodiment, the lipophilic electrolyte for use in selectively extracting heparin from a solution is dodecylguanidinium tetrakist(p-chlorophenyl)borate (DDG-TClPB).

Using the principles outlined above, it is also possible to determine lipophilic electrolytes having a lipophilic cation or lipophilic anion component that is selective for a specific polyion other than protamine or heparin. Accordingly, membranes incorporating such lipophilic electrolytes are also encompassed by the present invention.

The amount of lipophilic electrolyte present in the membrane according to the present invention can vary depending upon the physical properties of the membrane, which can limit the solubility of a salt in the membrane. Preferably, the lipophilic electrolyte is present at about 1 to about 15 weight percent based upon the total weight of the membrane. More preferably, the lipophilic electrolyte is present at about 5 to about 12 weight percent based upon the total weight of the membrane. In one preferred embodiment, the lipophilic electrolyte is present at about 10 weight percent based upon the total weight of the membrane.

In addition to the lipophilic electrolyte, the membrane according to the present invention can further comprise one or more plasticizers. The plasticizer facilitates mixture homogeneity and also helps control the flux of the polyion from the sample solution to the surface of the membrane and into the bulk of the membrane. Various plasticizers can be used in the membrane of the present invention including, but not limited to, plasticizers selected from the group consisting of 2-nitrophenyl octyl ether, dioctyl phthalate, dioctyl sebacate, dioctyl adipate, dibutyl sebacate, dibutyl phthalate, 1-decanol, 5-phenyl-1-pentanol, tetraundecyl benzhydrol 3,3',4,4'-tetracarboxylate, benzyl ether, dioctylphenyl phosphonate, tris(2-ethylhexyl) phosphate, and 2-nitrophenyl octyl ether. In a preferred embodiment according to the present invention, the plasticizer used in the membrane is 2-nitrophenyl octyl ether (NPOE).

It is generally preferred that that membrane of the present invention, in addition to the lipophilic electrolyte and the plasticizer, further comprise a substrate material to function as the bulk forming material of the membrane. Multiple substrates for use in forming a permeable membrane are known to those of skill in the art, and it is intended that the present invention encompass all such substrates.

In one embodiment, the substrate material is a polymeric film-forming material. The polymeric film-forming material according to this embodiment can be any polymeric material chemically compatible with the lipophilic electrolyte and the plasticizer. Further, the polymeric material should be capable of being formed into a film, such as through solvent casting. Polymeric materials useful according to the present invention include, as non-limiting examples, polyvinyl chloride, polyurethane, cellulose triacetate, polyvinyl alcohol, silicone rubber, and copolymers and terpolymers thereof. In one preferred embodiment, the polymeric film-forming material is polyvinyl chloride.

In one embodiment of the invention, the polyion-selective membrane comprises a lipophilic electrolyte in an amount of about 1 to about 15 weight percent. The membrane according to this embodiment further comprises about 28 to about 49.5 weight percent of a polymeric film-forming material and about 42.5 to about 66 weight percent of a plasticizer (all weights being based upon the total weight of the membrane). Preferentially, the polymeric film-forming material and the plasticizer are present in a ratio of about 1:1 to about 1:2 by weight.

In a preferred embodiment, the polyion-selective membrane comprises about 10 weight percent tetradodecylammonium 1,3-dinonylnaphthalene-4-sul-fonate, about 30 weight percent polyvinyl chloride, and about 60 weight percent 2-nitrophenyl octyl ether (all weights being based upon the total weight of the membrane).

A polyion-selective membrane according to one of the above embodiments can be prepared by solvent casting with an organic solvent, such as tetrahydrofuran (THF), suitable for casting into a thin film. Preferentially, the polymeric film-forming material, the plasticizer, and the lipophilic electrolyte are prepared as a homogeneous solution in the solvent. The solution can then be cast into a thin film. Once prepared as a thin film, the membrane can be cut to any specified size for later use in a polyion sensor. Rather than being formed into a thin film, the membrane solution can be applied to a substrate, such as an electrode, and allowed to dry on the electrode, thereby forming a film directly on the electrode.

According to one embodiment of the present invention, at least one of the lipophilic anion component and the lipophilic cation component can be covalently attached to the backbone structure of the polymeric film-forming material. For example, the anion component can be attached to the polymer chain through copolymerization through vinyl group linkage or some other suitable form of chemical reaction. Further, the lipophilic cation or anion component capable of attachment to the polymer structure can be a polyion-selective component or a counterion component.

In another embodiment, the substrate material is a microporous hydrophobic substrate. According to this embodiment, the plasticizer and the lipophilic electrolyte are formed into an admixture and then dispersed onto a microporous hydrophobic substrate, wherein the admixture of the plasticizer and the lipophilic electrolyte are taken up into the pores of the substrate and allowed to cure. The microporous hydrophobic substrate with the plasticizer and lipophilic electrolyte dispersed therein can then be processed for use in a polyion sensor. The microporous hydrophobic substrate according to one embodiment of the invention, can be selected from the group consisting of polyethylene, polypropylene, nylon, polyvinylidene fluoride, polycarbonate, polytetrafluoroethylene, acrylic copolymer, polyether sulfone, and copolymers and terpolymers thereof. According to one preferred embodiment, the microporous hydrophobic substrate is polyethylene. Particularly preferred as the microporous hydrophobic substrate are Celgard® membranes, available from Celgard, Inc., Charlotte, N.C. Celgard® membranes are polyethylene-based membranes available as flat sheet membranes and hollow fiber membranes.

In one preferred embodiment of the present invention, the polyion-selective membrane comprises a microporous hydrophobic substrate that has been contacted with an admixture comprising about 1 to about 15 weight percent of a lipophilic electrolyte comprising a lipophilic cation component and a lipophilic anion component and about 85 to about 99 weight percent of a plasticizer, based on the total weight of the mixture.

The present invention further provides a polyion-selective membrane electrode that is useful in an electrochemical cell. In one embodiment of the invention, the polyion-selective membrane electrode comprises a housing, a reference solution contained within the housing, and an electrode operatively positioned within the housing such that the electrode is in contact with the reference solution. Further, according to this embodiment, a polyion-selective membrane is disposed at one end of the housing. The membrane is in contact with the reference solution within the housing, and the membrane is operatively positioned for contacting a sample solution that is external to the housing. As noted above, the membrane comprises a lipophilic electrolyte having a lipophilic cation component and a lipophilic anion component, wherein at least one of the lipophilic anion and lipophilic cation components is selective for a specific polyion.

Any standard electrode could be used according to this embodiment of the invention, so long as the electrode is capable of incorporating a polyion-selective membrane as described above. In a particularly preferred embodiment of the present invention, the membrane electrode comprises a polyion-selective membrane incorporated into a standard electrode, such as a Philips electrode body (IS-561, Glasblserei Moller, Zurich, Switzerland).

The reference solution used in the electrode housing can be any electrolyte solution generally known to one of skill in the art as being useful. In one preferred embodiment, the electrolyte solution is a sodium chloride solution, in particular, a 1 M NaCl solution. Further, the electrode itself can be any type of electrode capable of use in electrochemical cells of potential and current values as described below. Particularly useful is a Ag/AgCl electrode.

The polyion-selective membrane incorporated into the membrane electrode is, according to one preferred embodiment, selective for protamine. Preferably, according to this embodiment, the lipophilic electrolyte used in the polyion-selective membrane is TDDA-DNNS.

When used with a membrane electrode, it is preferable that the polyion-selective membrane have a surface area of about 10 mm$^2$ to about 100 mm$^2$. More preferable is a surface area of about 20 mm$^2$ to about 50 mm$^2$. To achieve such surface areas, a thin film can be prepared, as described above, and the thin-film cut to the desired size, such as with a cork borer, for association with the electrode. It is further preferable that the polyion-selective membrane have an average thickness of about 10 μm to about 1000 μm, more preferably about 20 μm to about 300 μm.

The present invention is further directed to an electrochemical cell apparatus. In one embodiment, the electrochemical cell apparatus comprises a polyion-selective membrane electrode as previously described, a reference electrode electrically connected to the membrane electrode, and an electrochemical instrument operatively connected to the membrane electrode and the reference electrode.

One embodiment of an electrochemical cell apparatus according to the present invention is provided in FIG. 1, which shows an electrochemical cell apparatus 5 useful for measurement of a polyion species in a sample. FIG. 1 shows a polyion-selective membrane electrode 10, a reference electrode 30, and a counter electrode 50 operatively positioned in a testing sample container 60 having disposed therein a sample solution 65. The membrane electrode 10 comprises an electrode housing 15, a reference solution 17, and a reference electrode wire 21. Disposed at one end of the electrode housing 15 is a polyion-selective membrane 25 according to the present invention. The reference electrode 30, as shown in FIG. 1, is a double-junction electrode, although other types of reference electrodes could be used without departing from the invention. The reference electrode 30 includes an outer housing 33, an inner housing, 36, an outer housing reference solution 39, an inner housing reference solution 41, and a reference electrode wire 43.

As seen in FIG. 1, the polyion-selective membrane electrode 10, the reference electrode 30, and the counter electrode 50 are each operatively connected to an electrochemical instrument 75, which is further in communication with a controller device 90. The electrochemical instrument 75 is preferably a galvanostat-potentiostat. Accordingly, the electrochemical instrument is capable of controlling the current through the electrochemical cell at a preset value and is also capable of controlling the electrical potential between the working electrode (e.g. the polyion-selective membrane electrode 10) and the reference electrode 30 at a preset value. In performing the latter function, the electrochemical instrument 75 is capable of forcing whatever current is necessary between the working electrode (e.g. the polyion-selective membrane electrode 10) and the counter electrode 50 to keep the desired potential. In one particularly preferred embodiment, the electrochemical instrument 75 is a bipotentiostat, such as an AFCBP1 Bipotentiostat available from Pine Instruments (Grove City, Pa.).

The controller device 90, as shown in FIG. 1, is preferably a computer capable of carrying out an algorithm designed to automatically regulate the function of the electrochemical instrument 75 in controlling current, potential, or electrochemical activity desirable. The controller device 90 is also preferably capable of collecting data from the electrochemical instrument 75 and displaying the data visually to the user and/or storing the data. Of course, it is understood that both the electrochemical instrument 75 and the controller device 90 in FIG. 1 would be connected to a power supply (not shown).

The present invention is further directed to a method of measuring the concentration of a polyion species in a sample solution. The method generally comprises the following steps: a) providing a sample solution comprising a polyion species and a background electrolyte; b) contacting the sample solution with a polyion-selective membrane electrode having a membrane comprising a lipophilic electrolyte having a lipophilic cation component and a lipophilic anion component, wherein at least one of the lipophilic anion and lipophilic cation components is selective for the polyion species; c) contacting the sample with a reference electrode, the polyion-selective membrane electrode and the reference electrode being electrically connected; d) applying an external current pulse of fixed duration to a circuit comprising the polyion-selective membrane electrode and the sample solution, thereby driving transport of the polyion species from the sample solution into the membrane; e) measuring a potentiometric response during the current pulse between the polyion-selective membrane electrode and the reference electrode; and f) calculating the concentration of the polyion species as a function of the potentiometric response.

The external current pulse of fixed duration is preferentially applied for a duration of about 0.1 seconds to about 2 seconds. It is generally unnecessary to measure the potentiometric response for the full duration of the applied current pulse. Rather, it is preferred to measure the potentiometric response for only a portion of the duration of the applied external current pulse. In an especially preferred embodiment, the potentiometric response is measure during the last about 100 milliseconds of the fixed duration of the external current pulse.

The value of the potential measured in the above method depends upon the type of polyion present in the sample. For example, if a cation, such as protamine, is present, a cathodic current (negative) is applied to the cell. When the current is applied, the measured potential becomes more negative. When an anion, such as heparin, is present, an anodic current (positive) is applied to the cell. When the current is applied, the measured potential becomes more positive.

While the circuit to which the external current is applied generally comprises the polyion-selective membrane electrode and the sample solution, the circuit will also comprise one or more further components of the electrochemical cell. For example, in one embodiment according to the invention, the circuit further comprises a counter electrode. This embodiment would encompass electrochemical systems conventionally referred to as "three-electrode" electrochemical cells. Additionally, in another embodiment, the circuit further comprises a reference electrode. This embodiment encompasses electrochemical systems conventionally referred to as "two-electrode" electrochemical cells. Three-electrode systems are typically preferred to avoid degradation of the reference electrode that can occur when an external current is applied to such electrodes.

The absolute value of the potential measured in the above method will generally be expected to decrease with time due to the steadily increasing diffusion layer thickness in the membrane. As described above, when testing for the presence of a poly cation, such as protamine, a cathodic current is applied and a negative potential is observed. When protamine (or another poly cation) is present in the sample, the potential measured is significantly more positive than if the poly cation is not present. Conversely, when testing for the presence of a poly anion, an anodic current is applied and the observed potential is positive. If heparin (or another poly anion) is present in the sample, the measured potential would be expected to be significantly more negative than if the poly anion is not present. In both cases, the move toward a more positive or more negative charge is indicative of polyion extraction from the sample solution into the membrane. After sufficient time, the measurement would begin to fail due to the accumulation of the polyion in the membrane.

In a preferred embodiment of the present invention, the membrane is rehabilitated. According to this embodiment, the above method further comprises applying an external electrode potential to the polyion-selective membrane electrode and the reference electrode, thereby driving transport of the polyion species from the membrane. Once the membrane has been effectively stripped of the polyions, the polyion-selective membrane electrode can be used again for measurement of the polyions in the sample solution. Continuous, reversible detection of a polyion species becomes possible by repeatedly applying the pulse sequence comprising an external current pulse followed by an external potential pulse.

It is preferable that the external electrode potential that is applied to strip the polyions from the membrane is a baseline potential. The value of the baseline potential can vary depending upon the symmetry of the electrochemical cell. For example, in one embodiment, the membrane electrode and the reference electrode use identical electrodes and have inner reference solutions that are similar in composition to the sample solution. In such a preferred embodiment, the baseline potential is 0 V. Additional embodiments are also envisioned, wherein the electrodes exhibit less symmetry in varying degrees. In these additional embodiments, the baseline potential would be expected to vary from 0 V. The optimal baseline potential may be determined by disconnecting the electrochemical instrument (see FIG. 1), and replacing it with a high impedance voltmeter to measure the zero current potential between the membrane electrode and the reference electrode.

In order to effectively strip the polyions from the membrane, the external potential is preferably applied for a duration of time that is about 10 to about 20 times longer than the fixed duration of the external current pulse.

Further embodiments of the present invention are more distinctly described according to the following experimental examples.

Another aspect of the present invention is the detection of polyions, such as protamine, in a sample solution based on their direct relationship to an enzyme activity, such as trypsin. Enzyme activity can be detected if the enzyme is able to cleave polyions into shorter pieces, since these short pieces are generally not well detected by polyion sensors. Electrochemical detection, like the one disclosed in the present invention, has advantages over conventional spectrophotometric methods for monitoring enzyme activity in nontransparent, colored, or turbid samples.

One embodiment of this aspect of the present invention is the use of trypsin with protamine. Trypsin is an enzyme that cleaves proteins at the carboxyl side of the basic amino acids lysine and arginine. Since protamine is rich in arginine residues, trypsin will cleave protamine at these junctions. The initial rate of protamine decomposition was found to be directly proportional to trypsin activity when monitored using the electrochemical apparatus and protamine sensor disclosed in the present invention. The rate of change of the potential of the sensor signal as a function of time is the digestion of the protamine by the trypsin. This relationship can be extended to a variety of polyions and their corresponding enzymes.

Another embodiment of the present invention is application of a potential to clear the membrane to reuse it in the monitoring of enzyme activity, polyion concentration, and enzyme inhibitor activity. It should be noted that other biological and chemical activities can be monitored using the present invention.

In addition, the present invention can be used to monitor enzyme inhibitor activity in a sample solution. An enzyme inhibitor binds to an enzyme and effectively decreases the rate of reaction of the enzyme. The initial potential decrease upon addition of the mixture of enzyme and enzyme inhibitor is dependent on the concentration of enzyme inhibitor included in the sample solution.

One embodiment of this aspect of the present invention is for the enzyme trypsin and one of the following corresponding enzyme inhibitors: α1-antiproteinase inhibitor, α2-macroglobulin, aprotinin, and soybean inhibitor.

In yet another aspect of the present invention, potentiometric polyion sensitive electrodes can find application in the non-separation immunoassays. The immunoassay can employ labeled polyions or related enzymes as markers to detect analytes that can serve as a label through the competitive bidding of free analytes and marked analytes with antibodies.

EXPERIMENTAL

The present invention is more fully illustrated by the following examples, which are set forth to illustrate the present invention and are not to be construed as limiting thereof. Unless otherwise indicated, all percentages refer to percentages by weight based on the total weight of the polyion-selective membrane.

Example 1

Preparation of Protamine-Selective Membrane

The ability of a sensor incorporating a polyion-selective membrane according to the present invention to be used in an electrochemical cell was tested. A polycation-selective membrane was formulated, particularly to be selective for the polycation protamine. The membrane was formulated with 10 weight percent TDDA-DNNS in a 2:1 weight ratio mixture of 2-nitrophenyl octyl ether and polyvinyl chloride. The membrane was prepared by solvent casting with THF as the solvent. The mixture was allowed to dry into a film, and a protamine-selective membrane of about 200 μm thickness was prepared. The membrane was cut with a cork borer having a diameter of 6 mm to prepare membranes for incorporation into electrodes.

Example 2

Preparation of Protamine-Selective Membrane Electrodes

The protamine-selective membranes prepared in Example 1 were incorporated into electrodes. The electrode comprised a Philips electrode body (IS-561), an inner reference solution of 0.1 M NaCl, and an electrode wire of Ag/AgCl. The protamine-selective membrane electrodes were conditioned overnight before experimental use in a solution identical to the inner reference solution.

A set of 10 identical electrodes were prepared as described above and tested for consistency in a 0.1 M NaCl solution prior to actual experimental use. Testing showed an inter-electrode variability of +/−7 mV (standard deviation) at a given current in the range of 0 to −10 μA.

Figure 2:
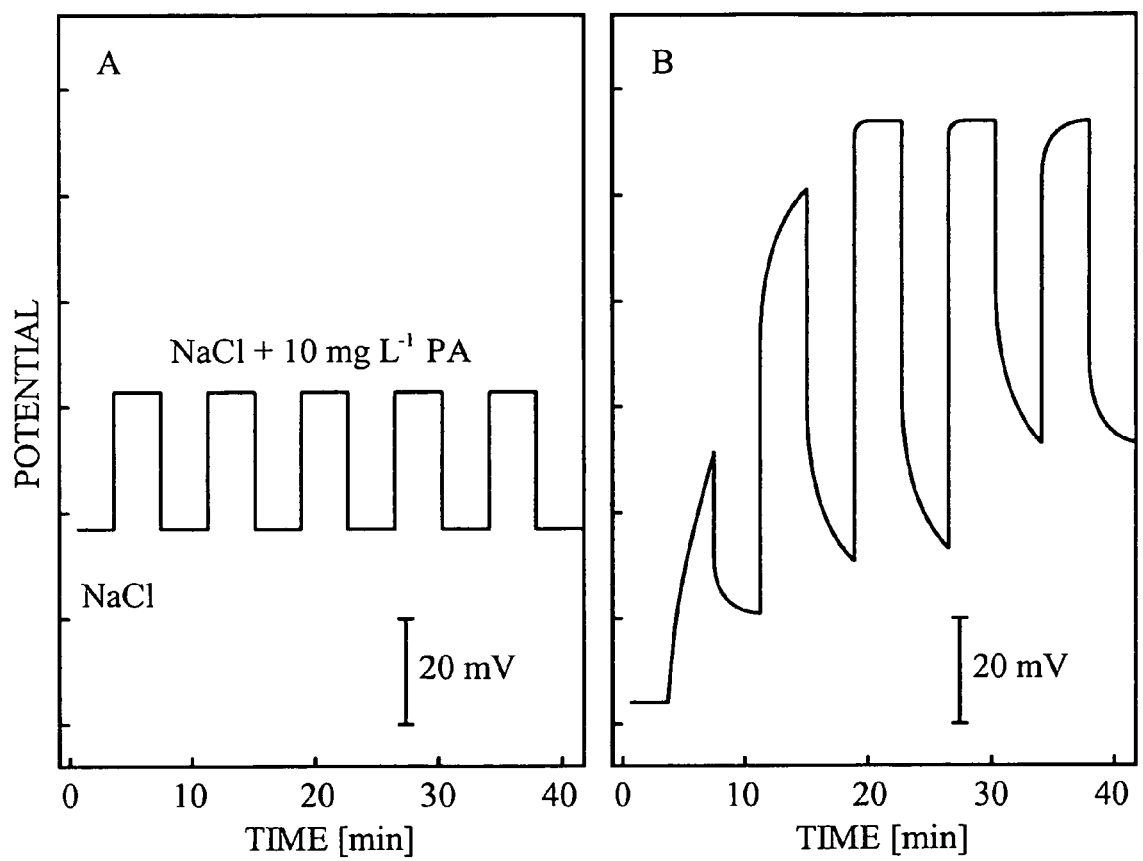
FIG. 2 is a chart illustrating electrode reproducibility upon alternating between 0.1 M NaCl and 0.1 M NaCl containing 10 mg/L protamine for (A) a polyion-selective membrane electrode according to the present invention and (B) a prior art ion-selective electrode.

The membrane electrodes were also tested to evaluate reversibility. The membrane was repeatedly exposed to two separate solutions, one containing 0.1 M NaCl, and one containing 0.1 M NaCl and 10 mg/L protamine. The same test was also performed using a prior art ion-selective electrode. The results of the test are shown in FIG. 2, wherein the protamine-selective electrode membrane of the present invention is illustrated in curve A and the prior art electrode is illustrated in curve B. As can be seen in both curves, a greater potential is observed when protamine is present. In curve A, the potential measurements were reproducible with a variation of +/−1 mV. In curve B, however shows variation of greater than 50 mV in as little as 5 cycles.

Example 3

Chronopotentiometric Responses for Samples with and without Protamine

A chronopotentiogram in 0.1 M NaCl with and without protamine was prepared. An electrochemical cell, such as that shown in FIG. 1, was set up using a protamine-selective membrane electrode as described in Example 2. The reference electrode was a double junction Ag/AgCl electrode with a 1 M LiOAc bridge electrolyte. The counter electrode was a platinum wire.

The voltammetric experiments were performed with an AFCBP1 Bipotentiostat (Pine Inst., Grove City, Pa.) controlled by a PCI-MIO-16E4 interface board and LabVIEW 5.0 Software (National Instruments, Austin, Tex.) on a Macintosh computer. Prior to the experiment the operation of the first electrode output of the bipotentiostat (K1) was switched to current control with potentiostatic control of output of the second working electrode (K2). In order to apply the current pulse, the working electrode was connected to the K1 output via an analog switch controlled by external software. When the baseline potential between current pulses was applied the working electrode was connected to the K2 output.

During the chronopotentiometric experiments, each applied constant current pulse of −3 μA (1 s duration) was followed by a constant potential pulse at 0 V (10 s duration).

Sampled potentials, which represented the sensor response, were obtained as the average value during last 100 ms of each current pulse. All experiments were conducted at laboratory ambient temperature (21.5±0.5° C.). Confidence intervals were computed at the 95% level.

The experiment was run in two samples. The first sample contained only 0.1 M NaCl, while the second sample contained 0.1 M NaCl and protamine (PA) at a concentration of 10 mg/L. The applied cathodic current of −3 μA lead to extraction of protamine into the membrane, and the observed potential is significantly different for the sample with protamine as compared to the sample without protamine. A current-time trace and potential-time trace for the chronopotentiometric experiment is provided in FIG. 3.

Example 4

Chronopotentiometric Responses for Samples with and without Protamine at Increased Levels A second chronopotentiogram in 0.1 M NaCl with and without protamine was prepared using the same experimental set up as provided in Example 2. During the chronopotentiometric experiments, each applied constant current pulse of −2 μA (1 s duration) was followed by a constant potential pulse at 0 V (15 s duration). Sampled potentials, which represented the sensor response, were obtained as the average value during last 100 ms of each current pulse. All experiments were conducted at laboratory ambient temperature (21.5±0.5° C.). Confidence intervals were computed at the 95% level.

The experiment was again run in two samples. The first sample contained only 0.1 M NaCl, while the second sample contained 0.1 M NaCl and protamine at a concentration of 50 mg/L. The applied cathodic current of −3 μA lead to extraction of protamine into the membrane, and the observed potential is significantly different for the sample with protamine as compared to the sample without protamine. A current-time trace and potential-time trace for the chronopotentiometric experiment is provided in FIG. 4.

During the potentiostatic resting pulse, the backdiffusion of the ions from the membrane can be observed. This diffusion is slower when protamine is present in the sample, indicating a difference in the diffusion behavior between sodium and protamine ions. When the current was integrated over the entire resting pulse of 15 s, the calculated charge corresponded to 90% of the applied charge during the current pulse.

Example 5

Figure 3:
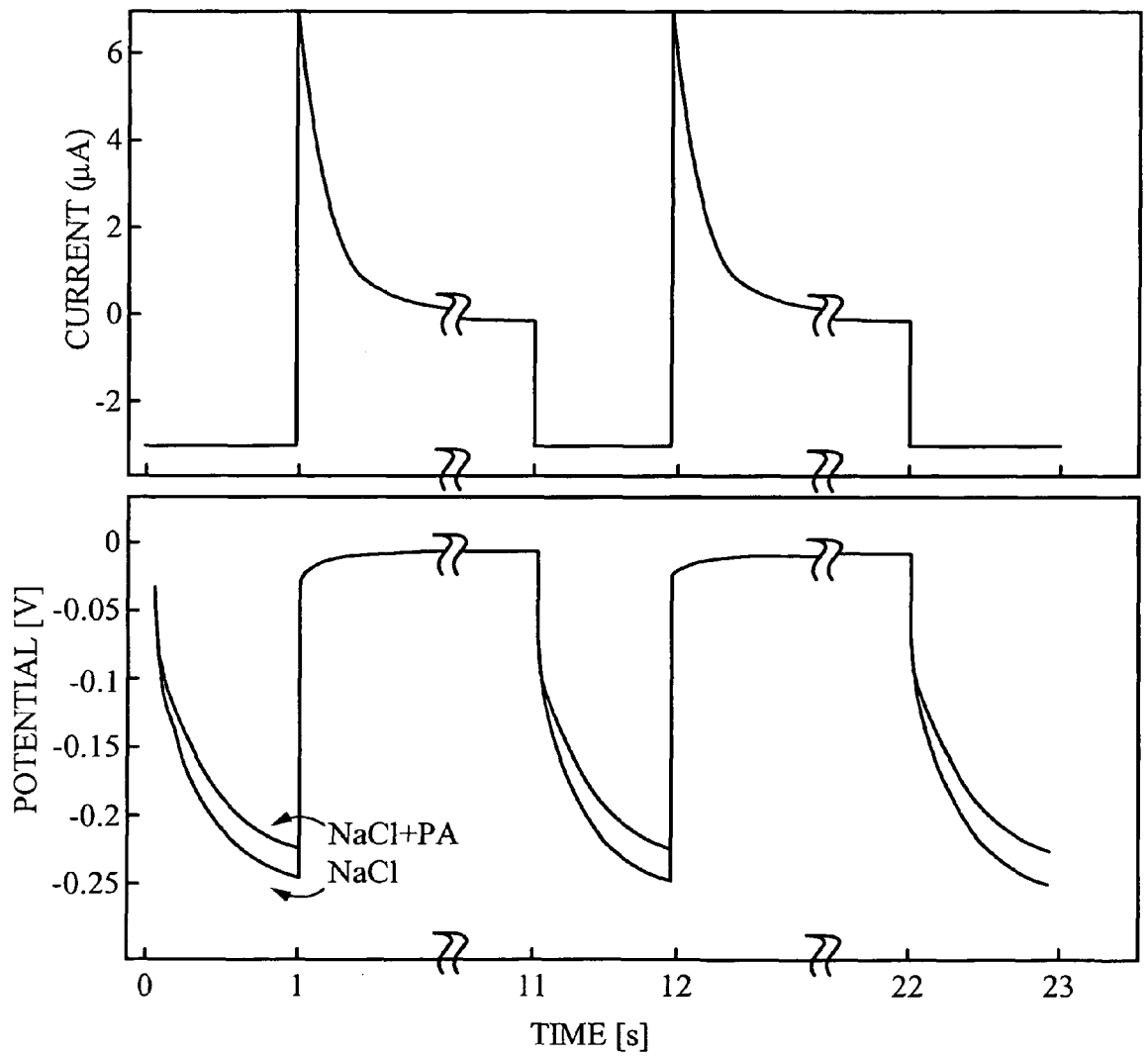
FIG. 3 is a chart illustrating current/time traces and potential/time traces for the pulsed galvanostatic measurement of a solution of 0.1 M NaCl and a solution of 0.1 M NaCl and 10 mg/L protamine using a method of measurement incorporating a polyion-selective membrane electrode according to the present invention.
Figure 4:
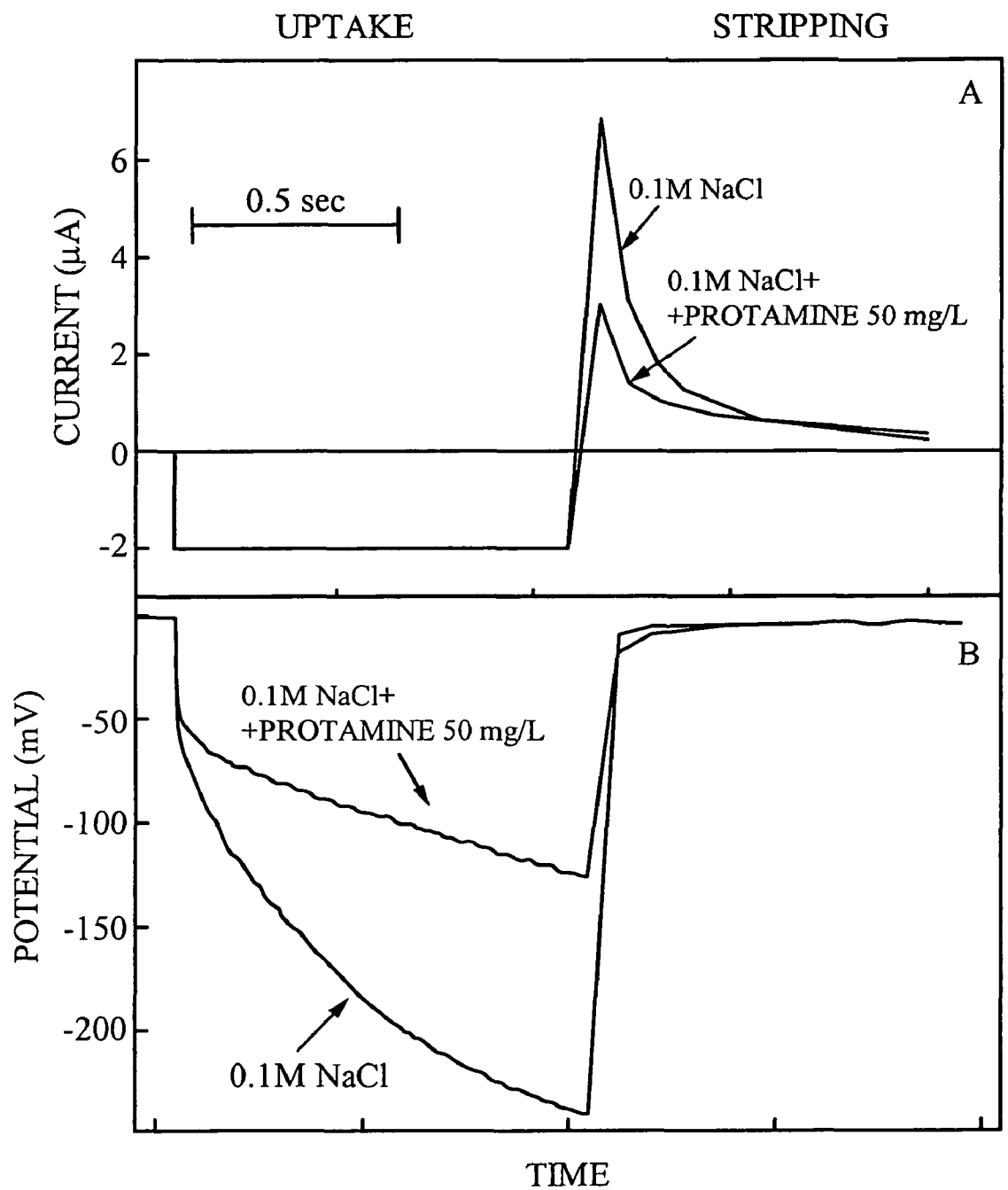
FIG. 4 is a chart illustrating current/time traces and potential/time traces for the pulsed galvanostatic measurement of a solution of 0.1 M NaCl and a solution of 0.1 M NaCl and 50 mg/L protamine using a method of measurement incorporating a polyion-selective membrane electrode according to the present invention.

Calibration Curves for Protamine Comparing Protamine-Selective Membrane Electrode of the Present Invention with Prior Art Polyion-Selective Membranes Continuous, reversible detection of protamine becomes possible by repeatedly applying the pulse sequence as illustrated in FIG. 3 and FIG. 4 and by sampling the potential reading at the end of each current pulse. Accordingly, it is possible to obtain a protamine calibration curve.

Figure 5:
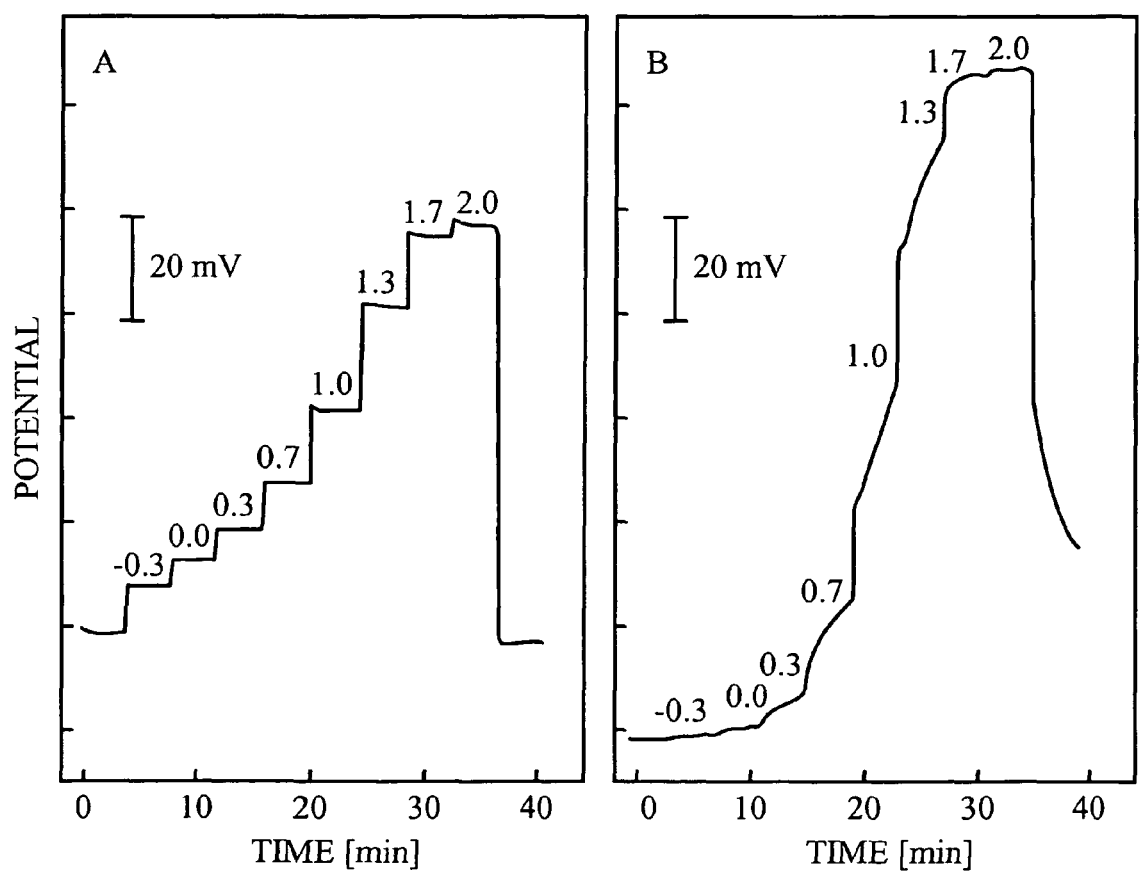
FIG. 5 is a chart illustrating calibration curves for protamine in 0.1 M NaCl using pulsed galvanostatic measurements and using (A) a polyion-selective membrane electrode according to the present invention and (B) a prior art ion-selective electrode.

Time traces for protamine calibration curves in 0.1 M NaCl were obtained using the methods described above in Examples 3 and 4. Curves were obtained using a protamine-selective membrane electrode as described in Example 2 and a prior art ion-selective electrode. A comparison of the two curves is provided in FIG. 5, wherein the curve obtained using the protamine-selective membrane electrode of the present invention is illustrated in curve A and the prior art electrode is illustrated in curve B. The strong potential drift observed in curve B originates from the poor control of the diffusion layer thickness on the membrane side. Logarithmic protamine concentrations (in mg/L) are indicated on the traces.

Example 6

Effect of Stirring on Sensor Response

Figure 6:
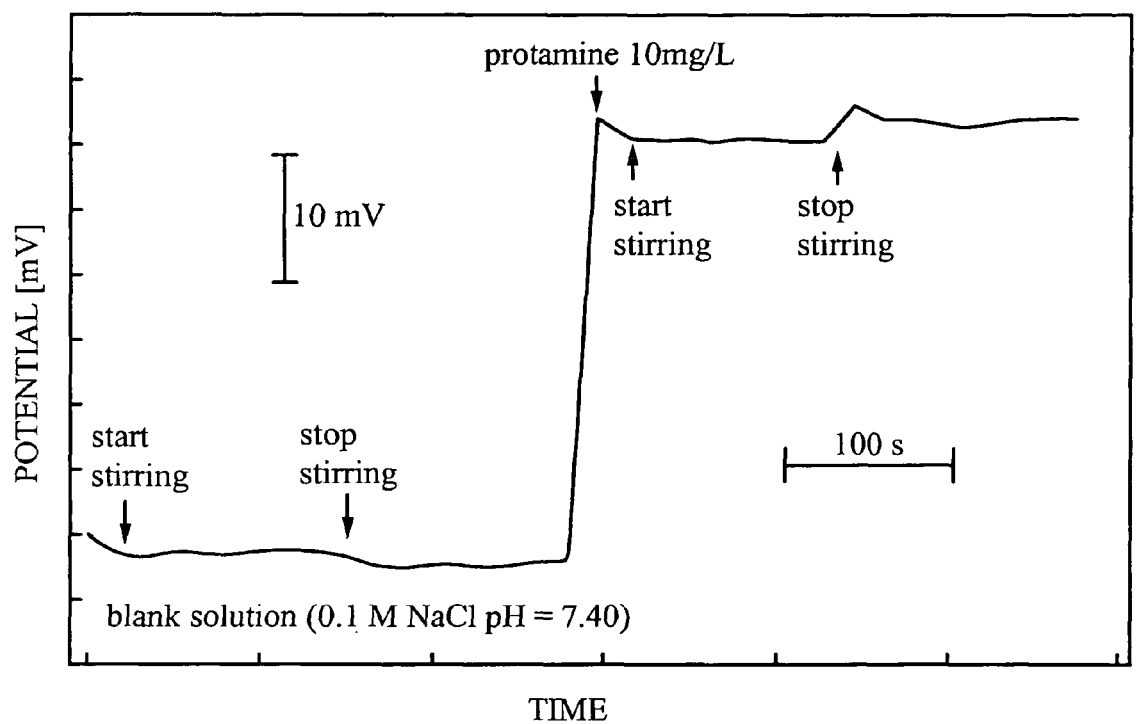
FIG. 6 is a chart illustrating the effect of stirring on the response of a polyion-selective membrane electrode according to the present invention when applying a cathodic current of −2 μA in blank solution of 0.1 M NaCl and in the presence of 10 mg/L of protamine.

With prior art potentiometric polyion sensors, the observed potentials are known to be strongly influenced by the rate of sample stirring, which alters the aqueous diffusion layer and hence the polyion flux to the membrane. In fact, recent work has confirmed a clear relationship between measuring range and rotation speed in a rotating electrode setup. To examine how stirring may affect the response of a polyion-selective membrane electrode according to the present invention in a galvanostatic pulse experiment, the potential was measured in unstirred solution and at a stirring rate of 100 rpm. A comparison of the two is provided in FIG. 6.

In contrast to potentiometric results with a heparin responsive membrane, where sudden stoppage of sample stirring caused the potential change of approximately 20 mV, the response of the pulse galvanostatic sensor of the present invention does not show significant influence on stirring rate. Potential difference between stirred and unstirred sample does not exceed 2-3 Mv.

Example 7

Effect of pH on Sensor Response

Figure 7:
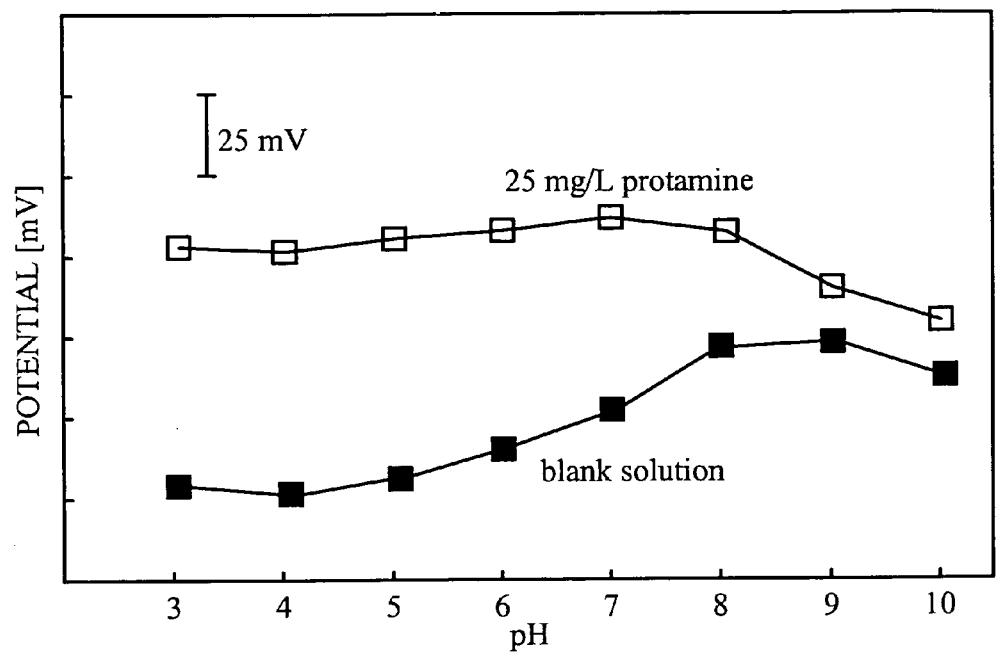
FIG. 7 is a chart illustrating the influence of a sample pH on the response of a polyion-selective membrane electrode according to the present invention at a cathodic current of −2 μA without protamine (lower curve) and with 25 mg/L of protamine added (upper curve)

Although the protamine sensor is intended to work in whole blood at the physiological pH of 7.4, the influence of pH on the sensor response was also examined. FIG. 7 provides observed potentials at a cathodic current of −2 μA. The lower trace is the observed potential with a blank solution comprising 0.1 M NaCl, 6.6 mmol citric acid, 11 mmol boric acid, and 10 mmol phosphoric acid, with the pH adjusted using 1 M NaOH. The upper trace is the observed potential for the same solution with 25 mg/L of protamine in the sample. Owing to the high protamine concentration, the difference between the two potentials may be regarded as the maximum sensor response, or potential window, in 0.1 M NaCl.

Example 8

Membrane Selectivity

Figure 8:
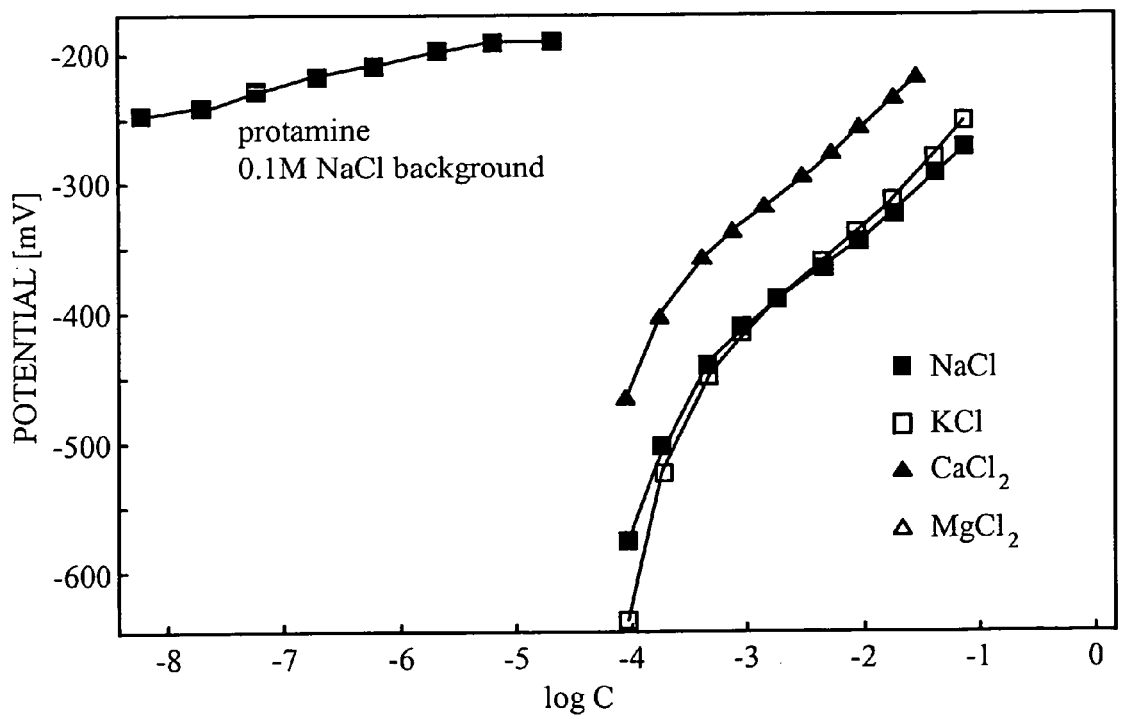
FIG. 8 is a chart illustrating calibration curves for a polyion-selective membrane electrode according to the present invention in pure solutions of NaCl, KCl, $MgCl_2$, $CaCl_2$ and of protamine in a 0.1 M NaCl background electrolyte solution.

The selectivity of the membrane was determined at pH 7.4 by recording separate calibration curves for the chloride salts of sodium, potassium, calcium and magnesium. Curves of the potential versus the log of the concentration of the salt are provided in FIG. 8. The resulting selectivity coefficients are in good agreement with those reported previously for DNNS based ISE membranes without additional ionophore. All slopes in the concentration range of 0.001 M-0.1 M were found to be slightly super-Nemstian (70-72 mV), which biases the selectivity coefficients to some extent. The slopes may likely be explained by the contribution of ion migration at the membrane interface on the basis of the Nernst-Plank equation, which has not yet been considered in the simplified theoretical model. The abrupt potential jump around $10^4$ M originates from depletion processes at the membrane surface. A protamine calibration curve in 0.1 M NaCl is also shown in FIG. 8. The higher potential readings demonstrate a strong preference of this membrane for protamine over all other tested cations.

Example 9

Effect of Background Electrolyte Concentration

Figure 9:
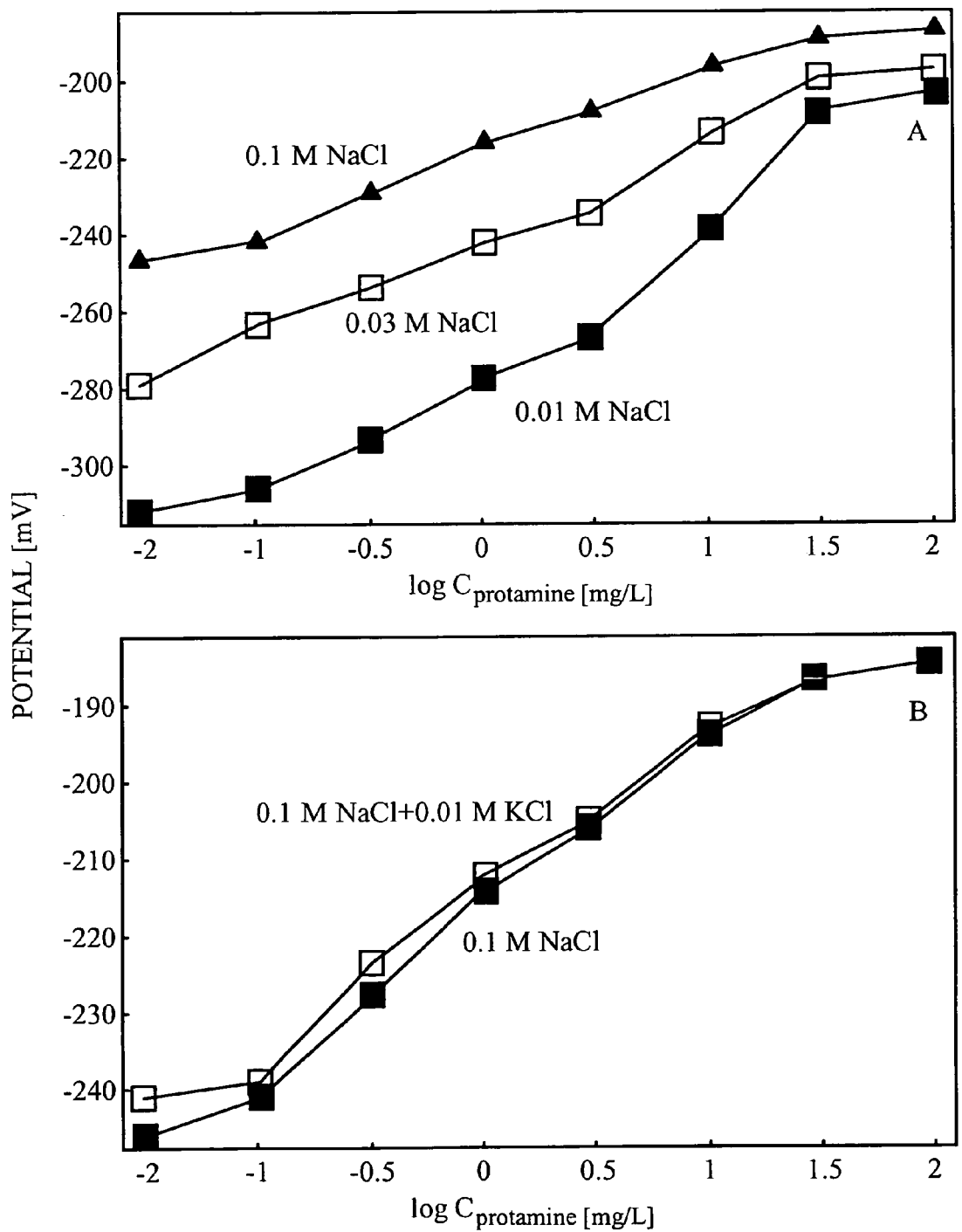
FIG. 9 provides two charts illustrating (A) calibration curves of protamine in the presence of different concentrations of supporting electrolyte (0.01 M NaCl, 0.03 M NaCl, and 0.1 M NaCl) and (B) the effect of KCl concentration on protamine calibration curves in 0.1 M NaCl with and without 0.01 M Kcl.

The background electrolyte concentration is expected to influence the protamine response curve because the response principle is based on a competitive extraction between the polyion and sodium ions. A lower sodium background concentration, for instance, is expected to give a larger potential range for the protamine response (see equation 10), and may also lead to a shift of the response to lower protamine concentrations (equation 10). FIG. 9A shows experimental protamine calibration curves in the presence of three sodium chloride concentrations, 10 mM, 30 mM, and 100 mM. The protamine potential range decreases with increasing NaCl concentrations.

The small influence of potassium on the protamine response is illustrated in FIG. 9B where two protamine calibration curves in 0.1 M NaCl with and without 10 mM KCl are shown. The maximum deviation of the response observed at low protamine concentration does indeed not exceed 5 mV.

Example 10

Calibration Curve for Protamine in Whole Blood

Figure 10:
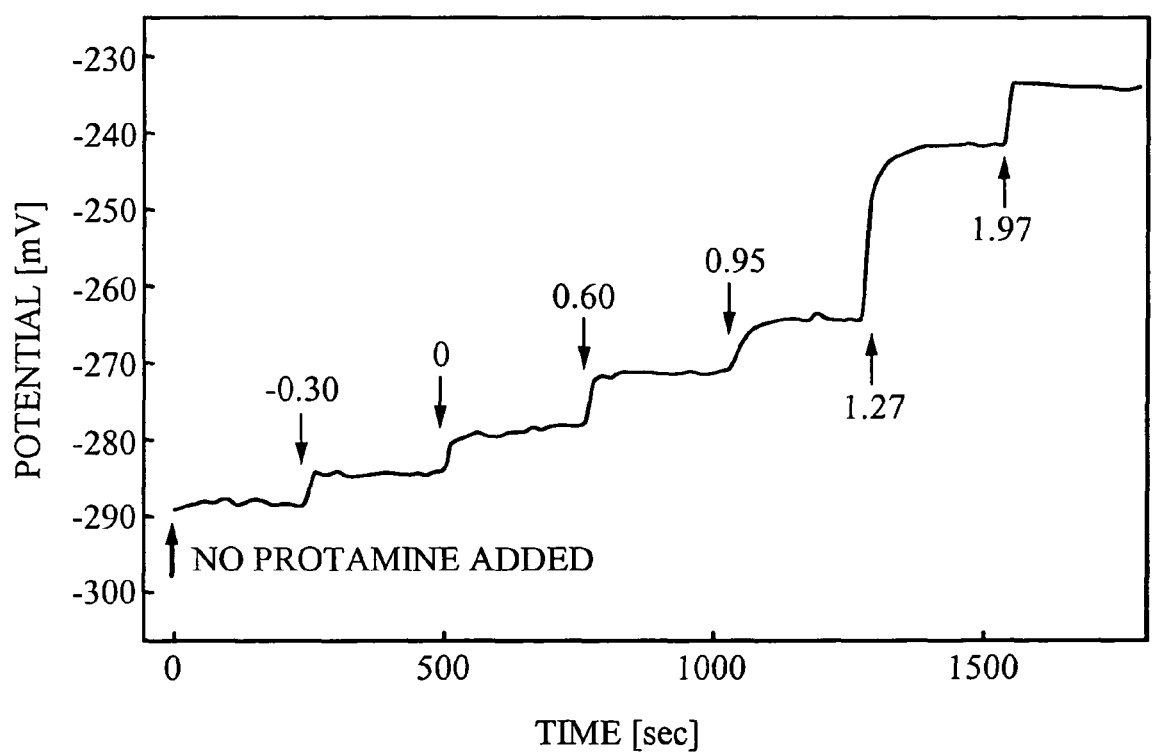
FIG. 10 is a chart illustrating amplitude-time behavior of potential for the protamine titration in whole blood using a polyion-selective membrane electrode according to the present invention.

FIG. 10 illustrates a calibration curve for protamine in whole blood and the corresponding potential-time trace for the calibration curve at the cathodic current of $-2$ $\mu$A. In whole blood the potential response range was found as about 60 mV, acceptably large for a practical determination of protamine in whole blood samples. Standard deviations of potentials increased up to 1.5 mV in comparison with 0.7 mV observed in buffered NaCl solutions. The results indicate that protamine concentrations as low as 0.5 mg/L can be determined with the current pulsed chronopotentiometric sensor.

Example 11

Titration of Whole Blood Samples

The experimental protocol can be used for determining heparin in blood via endpoint detection of a protamine titration, in analogy to previous work with potentiometric sensors. Small aliquots of heparin stock solution ($2 \times 10^{-5}$ M, 1.5 g/L) were added to whole blood samples in order to obtain different model concentrations of heparin in the range of 0.25 to 2 $\mu$M (0.6 to 4.5 kU/L), and titrated with 1 g/L protamine. The resulting titration curves are represented in FIG. 11A.

Each point was calculated as an average of 10 consecutive potential readings, giving standard deviations no larger than 1.5 mV. Reproducibility was evaluated by repeating each titration 4 times, giving deviations of starting and ending potentials of up to 7 mV from sample to sample, while the total change of potential during titrations remained the same. Since each collection tube contained 7.2 mg of the potassium salt of EDTA and the amount of blood collected in each tube varied from 2 to 4 mL, most of the deviation may be attributed to variations in the potassium concentration (see FIG. 9B).

Figure 11:
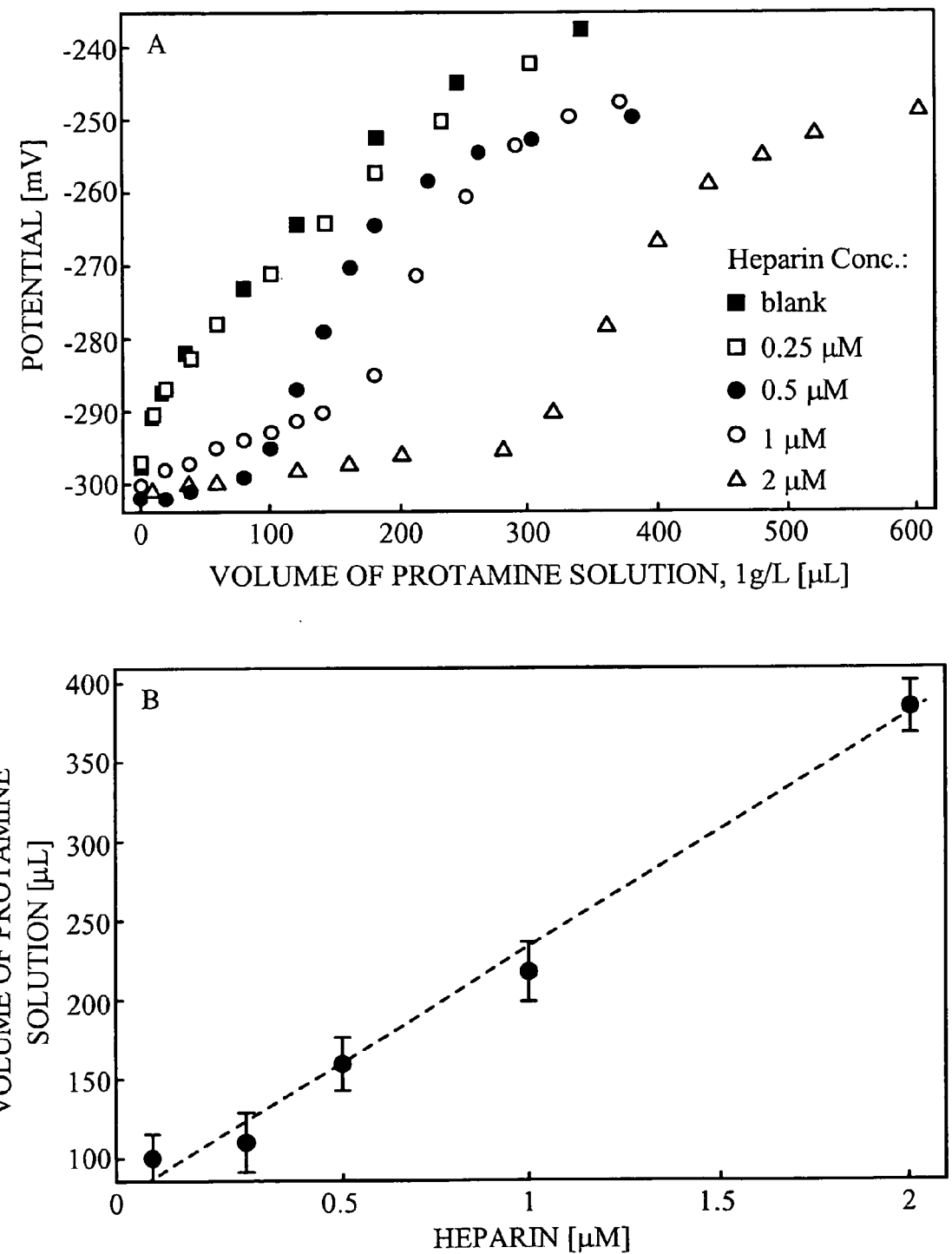
FIG. 11 is a chart illustrating (A) titration of whole blood samples, containing 0 mM, 0.25 mM, 0.5 mM, 1 mM, and 2 mM concentrations of heparin with 1 g/L of protamine solution using a polyion-selective membrane electrode according to the present invention and (B) a corresponding calibration curve for heparin-protamine titration in whole blood using a polyion-selective membrane electrode according to the present invention.

The observed endpoints are plotted in FIG. 11B as a function of the whole blood heparin concentration, and an expected linear relationship was found (correlation coefficient 0.995). The linear regression of this calibration curve yielded was determined as $c_{Heparin} = V(6.6 \pm 0.4) \times 10^{-3}$ M/L$-0.6$ $\mu$M.

Example 12

Lifetime and Sensor Stability

The lifetime and stability of the sensor are important parameters, especially if measurement is conducted in physiological media. Continuous pulsed chronopotentiomeric measurement in pH buffered 0.1 M NaCl containing 10 mg/L protamine for 3 hours, with 1 minute measurement intervals, gave no visible potential drift and a maximum potential variation of 2 mV. For whole blood samples, the titration curves shown in FIG. 11B were obtained with the same sensor and the total time of measurements in the blood exceeded 2.5 hours (for each point 10 potential measurements were collected). After exposure to blood the sensors were placed in buffered 0.1 M NaCl and the baseline potential was found to return to the initial value ($\pm 5$ mV for each sensor). The lifetime of sensors, defined as the time where baseline potential shifts did not exceed 20 mV, was at least 2 weeks, with a 10 h total exposure time to undiluted whole blood samples.

Example 13

Preparation of the Protamine-Selective Membrane Electrodes and Detection of Trypsin Activity and Inhibitor Activity The ion-selective membranes (200 $\mu$m thick) contained PVC and o-NPOE, 1:2 by weight and 5 wt % lipophilic salt TDDA-DNNS. The membranes were prepared by solvent casting, using THF as solvent. The membranes were cut with a cork borer (6-mm diameter) from the parent membrane and incorporated into a Philips electrode body (IS-561). The inner filling solution consisted of 0.1 M NaCl in 10 mM Tris-HCl buffer (pH=7.4) and was contacted with an internal Ag/AgCl electrode. The electrodes were conditioned overnight before experiments in the solution identical to inner filling solution. A double-junction Ag/AgCl electrode with a 1 M LiOAc bridge electrolyte was used as an external reference electrode.

Pulstrode measurements were conducted in a three-electrode cell system where the Philips body electrode (acted as a working electrode), external reference electrode and counter electrode (platinum wire) were immersed into the sample. The pulsed galvanostatic/potentiostatic technique was utilized in the control of the ion-selective membrane. During the experiments, each applied constant current pulse with current density of 0.5 $\mu$A/cm$^2$ (of 0.5-s duration) was followed by another constant zero current pulse (of 0.5-s duration), then a constant potential pulse (of 15-s duration) was added. Sampled potentials, which represent the sensor response, were obtained as the average value during the last 50 ms of the first current pulse.

Figure 12A:
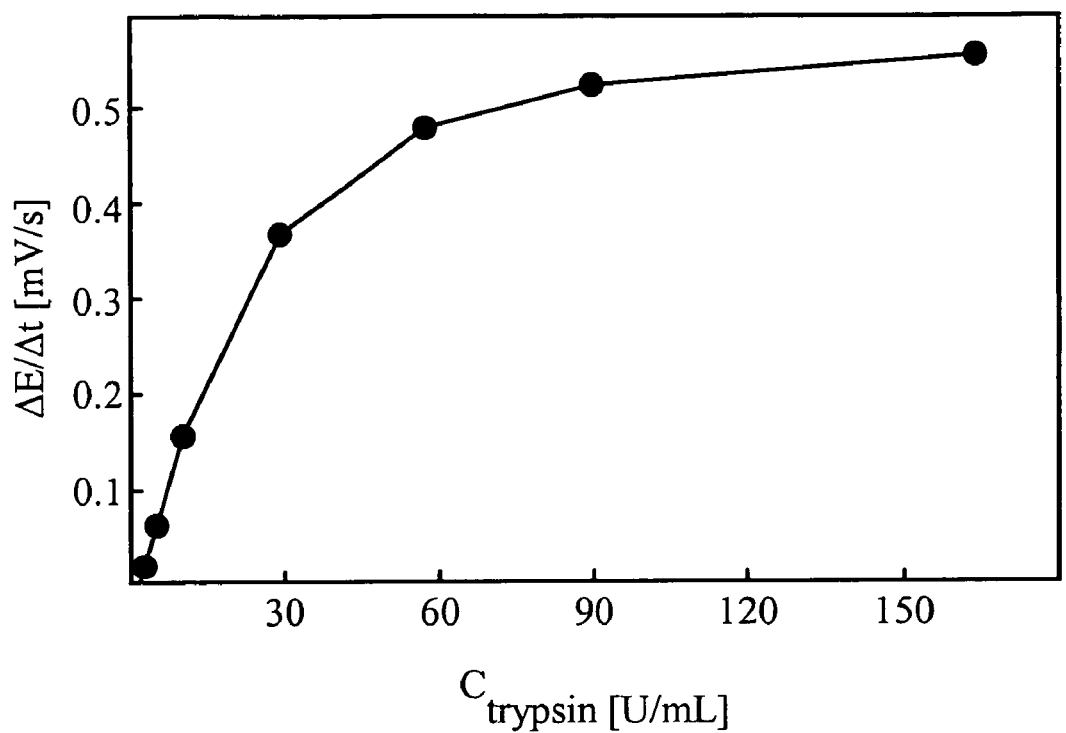
FIG. 12a is a chart illustrating the reaction rate of potential change (ΔE/Δt) immediately after the addition of trypsin, as a function of trypsin concentration.
Figure 12B:
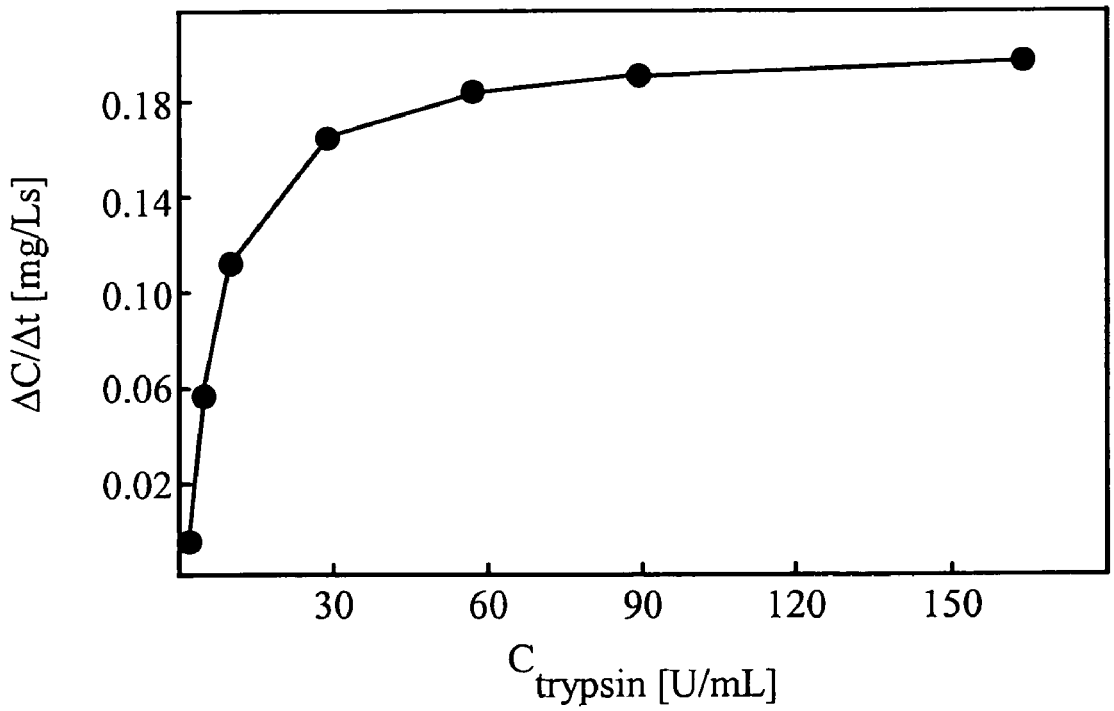
FIG. 12b is a chart illustrating the reaction rate of protamine concentration change (ΔC/Δt) immediately after the addition of trypsin, as a function of trypsin concentration.

Protamine has high content of basic amino acids, in which about 50% have arginine residues. Therefore, it is a good substrate for trypsin digestion reaction. As presented in FIG. 12a and FIG. 12b, the response of protamine decreased dramatically, upon addition of high concentration of protease trypsin, which is indicative of the occurrence of proteolytic reaction. All the experiments were performed using the same electrode, and the membrane is washed with the same buffer as background solution between measurements with different concentrations of trypsin. The total shift of baseline is about 7 mV, indicating the effective refreshment of sensing membrane.

The reaction rate of trypsin digestion of protamine can be estimated from the slope of the initial potential decrease upon trypsin addition. A gradually decreasing slope implied the rising reaction rate upon increased concentration of trypsin. Therefore, the protamine digestion is shown to be directly proportional to the trypsin activity in the sample.

Figure 13A:
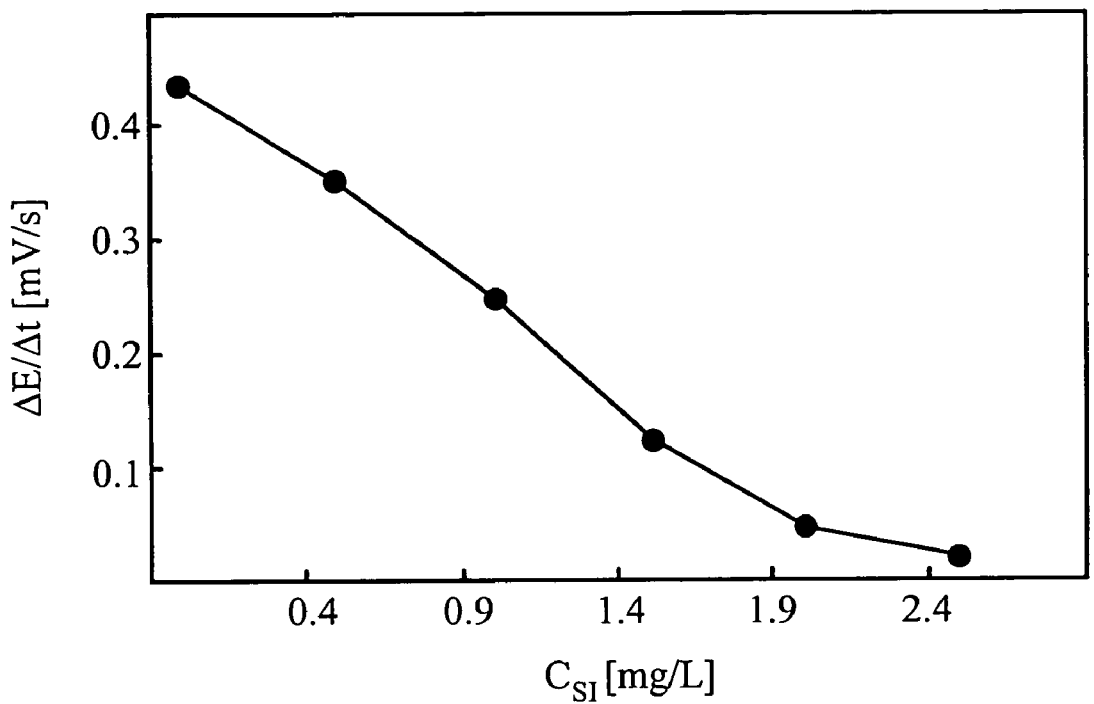
FIG. 13a is a chart illustrating the reaction rate of potential change (ΔE/Δt), immediately after the addition of trypsin and SI inhibitor, as a function of SI inhibitor concentration.
Figure 13B:
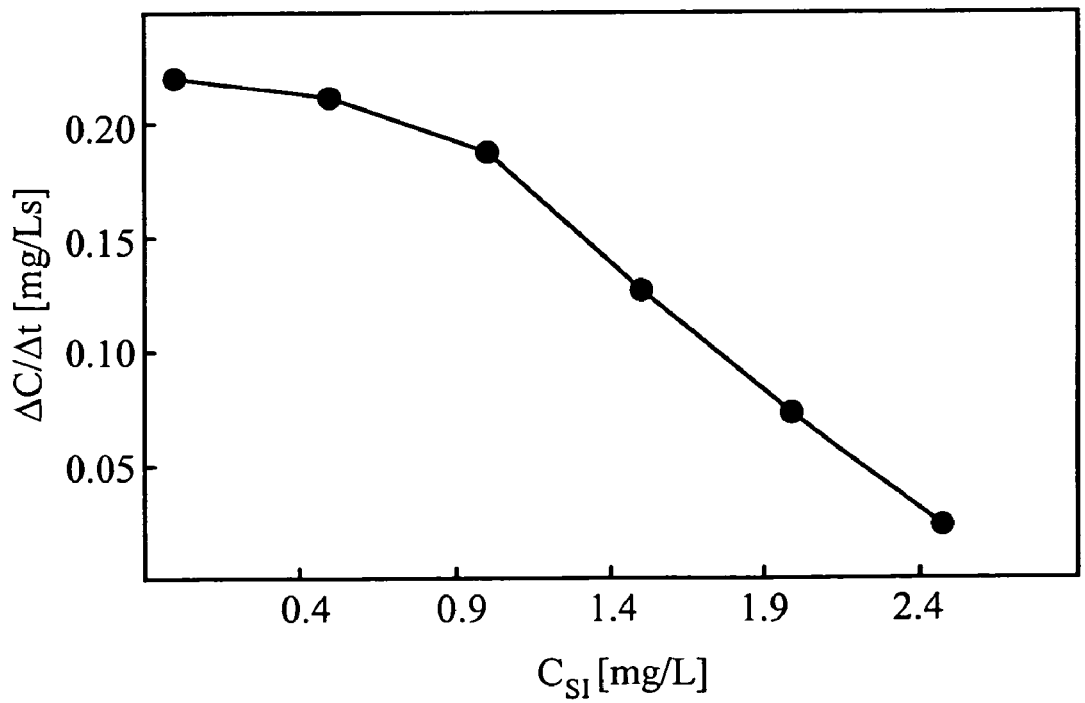
FIG. 13b is a chart illustrating the reaction rate of protamine concentration change (ΔC/Δt) immediately after the addition of trypsin and SI inhibitor, as a function of SI inhibitor concentration.

The activity of protease inhibitor is detected directly using potentiometric protamine sensor before and the trypsin-like inhibitor aprotinin was measured successfully in pretreated plasma samples. The activity of trypsin soybean inhibitor is estimated with Pulstrode protamine sensor. The inhibited reaction rate was assessed by the potential and protamine concentration change in the course of the first 96 seconds after addition the mixture of trypsin and soybean inhibitor with a fixed trypsin concentration of 50 units per milliliter. The results are illustrated versus the concentration of soybean inhibitor in FIGS. 13a and 13b. FIG. 13a shows the potential change versus the concentration of the soybean inhibitor, and FIG. 13b shows the protamine concentration change versus the concentration of the soybean inhibitor. The reaction rate was shown to decrease upon increased concentration of soybean inhibitor.

Many modifications and other embodiments of the inventions set forth herein will come to mind to one skilled in the art to which these inventions pertain having the benefit of the teachings presented in the foregoing description. Therefore, it is to be understood that the inventions are not to be limited to the specific embodiments disclosed and that modifications and other embodiments are intended to be included within the scope of the appended claims.

Although specific terms are employed herein, they are used in a generic and descriptive sense only and not for purposes of limitation.

That which is claimed:

1. A sensor comprising:
   an electrode positioned within a housing; and
   a membrane disposed at one end of the housing and in contact with a sample solution external to the housing, wherein the membrane comprises an electrolyte having a lipophilic cation component and a lipophilic anion component, the cation component being the counterion of the anion component, and further wherein the membrane detects a polyion concentration within the sample solution;
   wherein a rate of decomposition of the polyion concentration is directly proportional to an enzyme activity within the sample solution.

2. The sensor according to claim 1, wherein the electrode is a Ag/AgCl electrode.

3. The sensor according to claim 1, wherein the membrane has a surface area of about 10 mm$^2$ to about 100 mm$^2$.

4. The sensor according to claim 3, wherein the membrane has a surface area of about 20 mm$^2$ to about 50 mm$^2$.

5. The sensor according to claim 1, wherein the membrane has an average thickness of about 10 μm to about 1000 μm.

6. The sensor according to claim 5, wherein the membrane has an average thickness of about 20 μm to about 300 μm.

7. The sensor according to claim 1, wherein the polyion concentration is that of protamine.

8. The sensor according to claim 1, wherein the enzyme activity is that of trypsin.

9. The sensor of claim 1 wherein the membrane comprises substantially the same number of the cation components as of the anion components.

10. The sensor according to claim 1 wherein the cation component is equal to or greater than 1.0 weight percent of the weight of the membrane.

11. A reversible electrochemical cell apparatus comprising:
    a polyion-selective membrane electrode comprising a membrane, wherein the membrane comprises an electrolyte having a lipophilic cation component and a lipophilic anion component, the cation component being the counterion of the anion component, and further wherein the membrane detects a polyion concentration within the sample solution, and wherein a rate of decomposition of the polyion concentration is directly proportional to an enzyme activity within the sample solution; and
    means for applying a potential to clear the membrane.

12. The reversible electrochemical cell apparatus of claim 11, wherein the polyion concentration is that of protamine.

13. The reversible electrochemical cell apparatus of claim 11, wherein the enzyme activity is that of trypsin.

14. The reversible electrochemical cell apparatus of claim 11, wherein the means for applying a potential to clear the membrane is an external electrode potential applied between a reference electrode and the polyion-selective membrane electrode.

15. A reversible electrochemical cell apparatus comprising:
    a polyion-selective membrane electrode comprising a membrane, wherein the membrane comprises an electrolyte having a lipophilic cation component and a lipophilic anion component, the cation component being the counterion of the anion component, and further wherein the membrane detects a polyion concentration within the sample solution; and
    means for applying a potential between a reference electrode and the polyion-selective membrane electrode to clear the membrane.

16. A reversible electrochemical cell apparatus comprising:
    a polyion-selective membrane electrode comprising a membrane, wherein the membrane comprises an electrolyte having a lipophilic cation component and a lipophilic anion component, the cation component being the counterion of the anion component, and further wherein the membrane detects a polyion concentration within the sample solution, and wherein a rate of decomposition of the polyion concentration is directly proportional to an enzyme activity within the sample solution; and
    means for applying a potential between a reference electrode and the polyion-selective membrane electrode to clear the membrane.

17. The reversible electrochemical cell apparatus of claim 16, wherein the polyion concentration is that of protamine.

18. The reversible electrochemical cell apparatus of claim 16, wherein the enzyme activity is that of trypsin.

19. A sensor comprising:
    an electrode positioned within a housing; and
    a membrane disposed at one end of the housing and in contact with a sample solution external to the housing, wherein the membrane comprises an electrolyte having a lipophilic cation component and a lipophilic anion component, the cation component being the counterion of the anion component, and further wherein the membrane monitors an enzyme activity and a corresponding enzyme inhibitor activity in the sample solution.

20. The sensor according to claim 19, wherein the electrode is a Ag/AgCl electrode.

21. The sensor according to claim 19, wherein the membrane has a surface area of about 10 mm$^2$ to about 100 mm$^2$.

22. The sensor according to claim 21, wherein the membrane has a surface area of about 20 mm$^2$ to about 50 mm$^2$.

23. The sensor according to claim 19, wherein the membrane has an average thickness of about 10 μm to about 1000 μm.

24. The sensor according to claim 23, wherein the membrane has an average thickness of about 20 μm to about 300 μm.

25. The sensor according to claim 19, wherein the enzyme activity is that of trypsin.

26. The sensor according to claim 19, wherein the corresponding enzyme inhibitor activity is that of α1-antiproteinase inhibitor.

27. The sensor according to claim 19, wherein the corresponding enzyme inhibitor activity is that of α2-macroglobulin.

28. The sensor according to claim 19, wherein the corresponding enzyme inhibitor activity is that of aprotinin.

29. The sensor according to claim 19, wherein the corresponding enzyme inhibitor activity is that of a soybean inhibitor.

30. The sensor according to claim 19, wherein a potential decrease is dependent on the concentration of the corresponding enzyme inhibitor in the sample solution.

31. The sensor according to claim 19, further including an immunoassay for detecting analytes labeled by a marker.

32. The sensor according to claim 31, wherein the marker is a polyion.

33. The sensor according to claim 31, wherein the marker is an enzyme.

34. A liquid state sensor comprising:
an electrode positioned within a housing; and
a membrane disposed at one end of the housing and in contact with a sample solution external to the housing, wherein the membrane comprises a lipophilic electrolyte including a lipophilic cation component and a lipophilic anion component, the cation component being the counterion of the anion component, and further wherein the membrane detects a polyion concentration within the sample solution;
wherein a rate of decomposition of the polyion concentration is directly proportional to an enzyme activity within the sample solution.

* * * * *